US008682626B2

(12) United States Patent
Ionasec et al.

(10) Patent No.: US 8,682,626 B2
(45) Date of Patent: Mar. 25, 2014

(54) METHOD AND SYSTEM FOR COMPREHENSIVE PATIENT-SPECIFIC MODELING OF THE HEART

(75) Inventors: Razvan Ioan Ionasec, Lawrenceville, NJ (US); Ingmar Voigt, Erlangen (DE); Viorel Mihalef, Keasbey, NJ (US); Sasa Grbic, Erlangen (DE); Dime Vitanovski, Erlangen (DE); Yang Wang, Plainsboro, NJ (US); Yefeng Zheng, Dayton, NJ (US); Bogdan Georgescu, Plainsboro, NJ (US); Dorin Comaniciu, Princeton Junction, NJ (US); Puneet Sharma, Rahway, NJ (US); Tommaso Mansi, Westfield, NJ (US)

(73) Assignee: Siemens Aktiengesellschaft, München (DE)

( * ) Notice: Subject to any disclaimer, the term of this patent is extended or adjusted under 35 U.S.C. 154(b) by 384 days.

(21) Appl. No.: 13/091,076

(22) Filed: Apr. 20, 2011

(65) Prior Publication Data

US 2012/0022843 A1 Jan. 26, 2012

Related U.S. Application Data

(60) Provisional application No. 61/366,294, filed on Jul. 21, 2010, provisional application No. 61/383,942, filed on Sep. 17, 2010, provisional application No. 61/409,633, filed on Nov. 3, 2010.

(51) Int. Cl.
*G06G 7/48* (2006.01)
(52) U.S. Cl.
USPC ............................... 703/6; 382/128; 600/416
(58) Field of Classification Search
USPC ........... 703/1, 2, 9, 6; 382/128, 131; 600/416, 600/500, 523
See application file for complete search history.

(56) References Cited

U.S. PATENT DOCUMENTS 5,687,737 A * 11/1997 Branham et al. ............... 600/523
2005/0187461 A1* 8/2005 Murphy et al. ............... 600/416
(Continued)

OTHER PUBLICATIONS

Taylor et al., "Patient Specific modeling of Cardiovascular mechanics", Stanford University, 2009.*
Mihelf et al., "Atrioventricular blood flow simulation based on patient specific data", Functional imaging and modeling of heart, 2009.*
Lorenz et al., "A comprehensive shape model of heart", Medical image analysis, 2006.*

(Continued)

*Primary Examiner* — Kandasamy Thangavelu
(74) *Attorney, Agent, or Firm* — Michele L. Conover

(57) ABSTRACT

A method and system for patient-specific modeling of the whole heart anatomy, dynamics, hemodynamics, and fluid structure interaction from 4D medical image data is disclosed. The anatomy and dynamics of the heart are determined by estimating patient-specific parameters of a physiological model of the heart from the 4D medical image data for a patient. The patient-specific anatomy and dynamics are used as input to a 3D Navier-Stokes solver that derives realistic hemodynamics, constrained by the local anatomy, along the entire heart cycle. Fluid structure interactions are determined iteratively over the heart cycle by simulating the blood flow at a given time step and calculating the deformation of the heart structure based on the simulated blood flow, such that the deformation of the heart structure is used in the simulation of the blood flow at the next time step. The comprehensive patient-specific model of the heart representing anatomy, dynamics, hemodynamics, and fluid structure interaction can be used for non-invasive assessment and diagnosis of the heart, as well as virtual therapy planning and cardiovascular disease management. Parameters of the comprehensive patient-specific model are changed or perturbed to simulate various conditions or treatment options, and then the patient specific model is recalculated to predict the effect of the conditions or treatment options.

50 Claims, 25 Drawing Sheets

(56) References Cited

U.S. PATENT DOCUMENTS

| | | | |
|---|---|---|---|
| 2007/0014452 A1* | 1/2007 | Suresh et al. | 382/128 |
| 2008/0077032 A1* | 3/2008 | Holmes et al. | 600/523 |
| 2008/0101676 A1 | 5/2008 | Zheng et al. | |
| 2008/0262814 A1 | 10/2008 | Zheng et al. | |
| 2008/0275351 A1* | 11/2008 | Kirchberg et al. | 600/500 |
| 2009/0123050 A1* | 5/2009 | Ionasec et al. | 382/131 |
| 2009/0154785 A1* | 6/2009 | Lynch et al. | 382/131 |
| 2010/0070249 A1* | 3/2010 | Ionasec et al. | 703/2 |
| 2010/0145661 A1* | 6/2010 | Ecabert et al. | 703/1 |
| 2010/0239147 A1 | 9/2010 | Vitanovski et al. | |
| 2010/0239148 A1 | 9/2010 | Zheng et al. | |
| 2010/0280352 A1 | 11/2010 | Ionasec et al. | |
| 2011/0060576 A1 | 3/2011 | Sharma et al. | |
| 2011/0295579 A1* | 12/2011 | Tang et al. | 703/9 |
| 2012/0027278 A1* | 2/2012 | Chaney et al. | 382/131 |

OTHER PUBLICATIONS

Dey et al., "Estimation of cardiac respiratory motion by semi-automatic segmenation and registration . . . 4D CT cardiac datasets", IEEE 2009.*

Moreno et al., "Optimized computational functional imaging of arteries", High Performance computing for computational science, 2008.*

Yang et al., "3D Ultrasound Tracking of the Left Ventricles Using One-Step Forward Prediction and Data Fusion of Collaborative Trackers", CVPR 2008.

Ionasec et al., "Patient-Specific Modeling and Quantification of the Aortic and Mitral Valves from 4D Cardiac CT and TEE", IEEE Transactions on Medical Imaging, 2010.

Ionasec et al., "Robust Motion Estimation Using Trajectory Spectrum Learning: Application to Aortic and Mitral Valve Modeling from 4D TEE", Proceedings of 12th IEEE International Conference on Computer Vision, 2008, pp. 1601-1608.

* cited by examiner

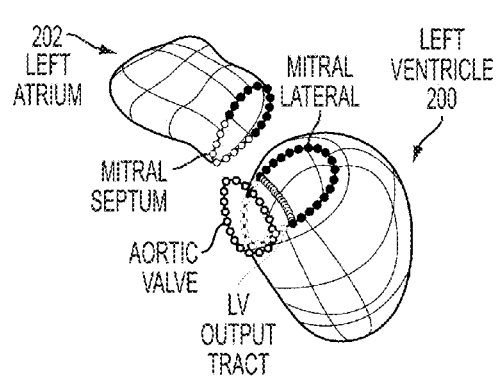
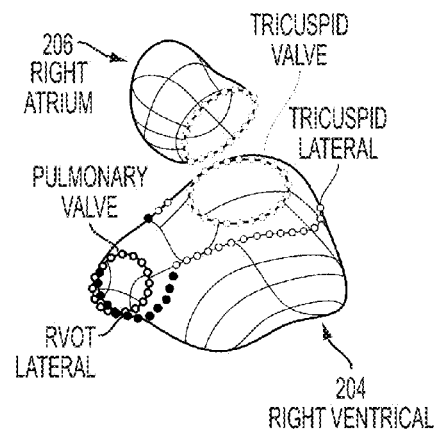
FIG. 2A
FIG. 2B
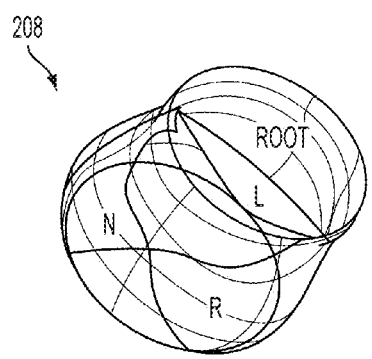
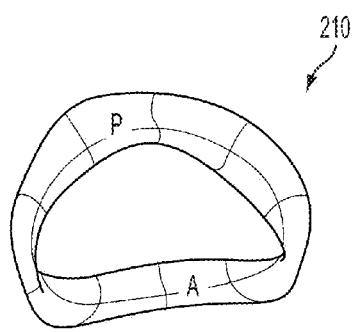
FIG. 2C
FIG. 2D
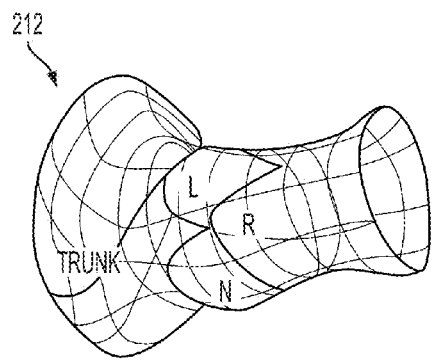
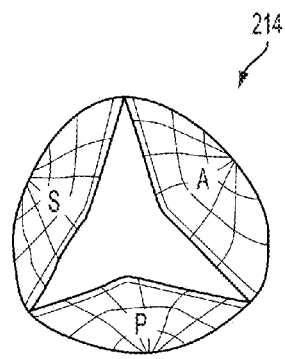
FIG. 2E
FIG. 2F

METHOD AND SYSTEM FOR COMPREHENSIVE PATIENT-SPECIFIC MODELING OF THE HEART

This application claims the benefit of U.S. Provisional Application No. 61/366,294, filed Jul. 21, 2010, U.S. Provisional Application No. 61/383,942, filed Sep. 17, 2010, and U.S. Provisional Application No. 61/409,633, filed Nov. 3, 2010, the disclosures of which are herein incorporated by reference.

BACKGROUND OF THE INVENTION

The present invention relates to modeling the heart using medical images, and more particularly, to comprehensive patient-specific modeling of the heart based on 4D medical image data.

Cardiac disease is the leading cause of death for men and women in the United States and accounts no less than 30% of deaths worldwide. Although medical advances in recent years have provided important improvements in the diagnosis and treatment of complex cardiac diseases such as valvular disease, thoracic aortic aneurysm, and Tetralogy of Fallot, the incidence of premature morbidity and morality is still large. Medical imaging modalities, such as computed tomography (CT), magnetic resonance (MR), rotational X-ray, and Ultrasound, can be used to acquire large amounts of morphological and functional image data with a high temporal-spatial resolution. However, due to a lag in data understanding capabilities, physicians are forced to make vital decisions based on measurements and methods that are limited in scope. These limitations are at least in part due to the lack of efficient and accurate estimation of patient-specific parameters describing the heart-aortic anatomy, physiology, and hemodynamics, as well as the lack of disease progression models.

BRIEF SUMMARY OF THE INVENTION

The present invention provides a method and system for comprehensive patient-specific modeling of the heart from 4D medical image data. In particular, embodiments of the present invention provide patient-specific modeling of the whole heart anatomy, dynamics, hemodynamics, and fluid structure interaction from 4D medical image data.

The anatomy and dynamics of the heart are determined by estimating patient-specific parameters of a physiological model of the heart from the 4D medical image data for a patient. The patient-specific anatomy and dynamics are used as input to a 3D Navier-Stokes solver that derives realistic hemodynamics, constrained by the local anatomy, along the entire heart cycle. Fluid structure interactions are determined iteratively over the heart cycle by simulating the blood flow at a given time step and calculating the deformation of the heart structure based on the simulated blood flow, such that the deformation of the heart structure is used in the simulation of the blood flow at the next time step. The comprehensive patient-specific model of the heart representing anatomy, dynamics, hemodynamics, and fluid structure interaction can be used for non-invasive assessment and diagnosis of the heart, as well as virtual therapy planning and cardiovascular disease management.

In one embodiment of the present invention, a patient-specific 4D anatomical model of the heart is generated from 4D medical imaging data. Blood flow in the heart is then simulated by solving Navier-Stokes equations constrained by the patient-specific 4D anatomical model at each of a plurality of time steps in a heart cycle using a level set framework.

In another embodiment of the present invention, a patient-specific 4D anatomical model of the heart is generated from 4D medical imaging data. Blood flow is simulated in at least one heart component of the patient-specific 4D anatomical model at a current time step by solving Navier-Stokes equations constrained by the location of the at least one heart component at the current time step using a level set framework. A deformation of the at least one heart component is calculated at the current time step based on the simulated blood flow at the current time step. The simulating and calculating steps are repeated for a plurality of time steps, and the current location of the at least one heart component at the current time step is determined at least in part based on the deformation of the at least one heart component calculated at a previous time step.

In another embodiment of the present invention, a comprehensive patient-specific 4D model of the heart is generated from 4D medical imaging data. A portion of the comprehensive patient-specific 4D model is adjusted to simulate a condition, such as a disease or a therapy. The comprehensive patient-specific 4D model of the heart is then regenerated to simulate the effect of the adjusted portion on the comprehensive patient-specific 4D model.

These and other advantages of the invention will be apparent to those of ordinary skill in the art by reference to the following detailed description and the accompanying drawings.

BRIEF DESCRIPTION OF THE DRAWINGS

FIGS. 2A-2F illustrate cardiac models for various heart components according to an embodiment of the present invention;

DETAILED DESCRIPTION

The present invention relates to comprehensive patient-specific modeling of the heart from a sequence of volumetric data, such as computed tomography (CT), magnetic resonance imaging (MRI), and echocardiography data. Such sequences of volumetric data, also referred to herein as 4D image data or 4D images, are sequences taken over a period of time to cover one or more cardiac cycles, in which each frame is a 3D image (volume). Embodiments of the present invention are described herein to give a visual understanding of the heart modeling method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a method and system for patient-specific modeling of the whole heart anatomy, dynamics, hemodynamics, and fluid structure interaction from 4D medical image data. The anatomy and dynamics of the heart are determined by estimating patient-specific parameters of a physiological model of the heart from the 4D medical image data for a patient. The patient-specific anatomy and dynamics are used as input to a 3D Navier-Stokes solver that derives realistic hemodynamics, constrained by the local anatomy, along the entire heart cycle. Fluid structure interactions are determined iteratively over the heart cycle by simulating the blood flow at a given time step and calculating the deformation of the heart structure based on the simulated blood flow, such that the deformation of the heart structure is used in the simulation of the blood flow at the next time step. The comprehensive patient-specific model of the heart representing anatomy, dynamics, hemodynamics, and fluid structure interaction can be used for non-invasive assessment and diagnosis of the heart, as well as virtual therapy planning and cardiovascular disease management.

Figure 1:
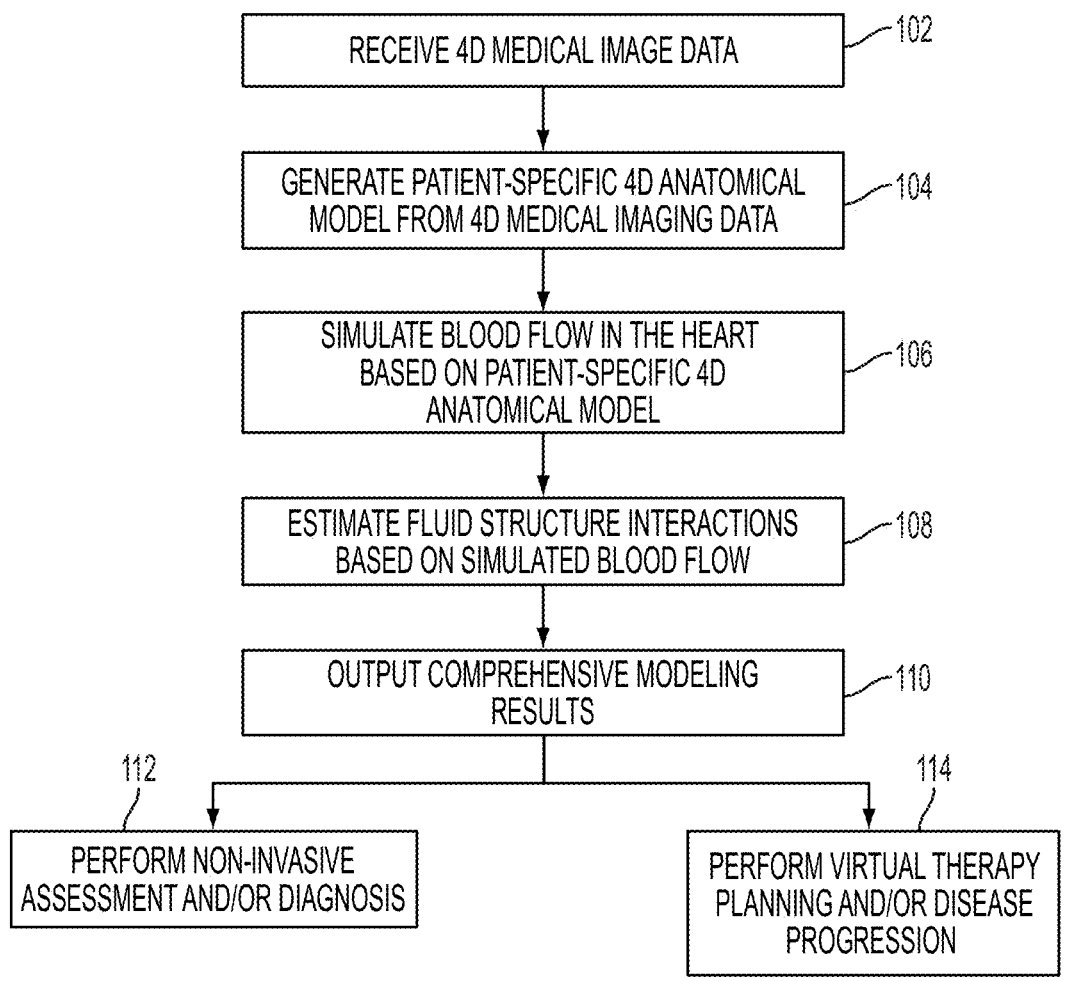
FIG. 1 illustrates a method for comprehensive patient-specific modeling of the heart according to an embodiment of the present invention.

FIG. 1 illustrates a method for comprehensive patient-specific modeling of the heart according to an embodiment of the present invention. The method of FIG. 1 transforms image data representing a coronary region of a patient into a patient-specific anatomical model of the heart and uses the patient-specific heart model to simulate blood flow and fluid structure interactions of the heart.

Referring to FIG. 1, at step 102, 4D medical image data is received. In particular, at least one sequence of volumetric image data is received. The sequence of volumetric image data can be a sequence of 3D images (volumes) acquired over a certain time period. For example, such a 4D image data (3D+time) can be acquired over a one full heart cycle. One or more sequences can be received using various medical imaging modalities. For example, according to various embodiments of the present invention, 4D CT data, 4D echocardiography, and/or 4D magnetic resonance (MR) image data can be received, as well as other types of image data. The image data can be received directly from one or more image acquisition devices, such as a CT scanner, an ultrasound device, or an MR scanner. It is also possible that previously stored image data be loaded, for example from a memory or storage of a computer system or some other computer readable storage medium.

At step 104, a patient-specific 4D anatomical model of the heart is generated from the received 4D image data. In particular, the 4D anatomical model is a multi-component model having multiple cardiac components, including as the chambers (left ventricle, left atrium, right ventricle, and right atrium), the heart valves (aortic valve, mitral valve, tricuspid valve, and pulmonary valve), and the aorta. Such a comprehensive model of the heart is used to capture a large variety of morphological, functional, and pathological variations. A modular and hierarchical approach can be used to reduce anatomical complexity and facilitate an effective and flexible estimation of individual anatomies. Embodiments of the present invention use a heart model that is anatomically compliant and maintains a consistent parameterization across the cardiac cycle and different patients by utilizing physiological-driven constraints and sampling schemes.

The global dynamic variation of each heart chamber and valve is parameterized as a temporal dependent similarity transform, which defines the translation, the quaternion representation of the rotation, the similarity transform scaling factors, and the temporal position in the cardiac cycle. In an advantageous embodiment, a set of 152 anatomical landmarks for the heart chambers and 33 anatomical landmarks for the heart valves are used to parameterize the complex and synchronized motion pattern of all heart anatomies. Thereby, each landmark is described by a trajectory in a three dimensional space, normalized by the temporal dependent similarity transform. The final model is completed with a set of nine dense surface meshes to represent the chambers and an additional set of 13 structures for the valves. Each mesh is sampled along anatomical grids of vertices defined through the landmarks.

FIGS. 2A-2F illustrate cardiac models for various heart components according to an embodiment of the present invention. In particular, FIGS. 2A-2F show the anatomical definition for the various components of the anatomical heart model. The parameters of these anatomical models are estimated for a particular patient over a cardiac cycle based on the 4D image data.

FIG. 2A shows models for the left ventricle 200 and the left atrium 202. The left ventricle 200 is constructed from 78 landmarks (16 mitral lateral control points, 15 mitral septum control points, 16 left ventricle output tract control points, and 32 aortic valve control points) and four surface geometries (LV epicardium, LV endocardium, and LV output tract). The left atrial surface 202 is connected to the left ventricle 200 via the aortic valve control points.

FIG. 2B shows models for the right ventricle 204 and right atrium 206. The right ventricle 204 is constructed from 74 landmarks (16 tricuspid lateral control points, 15 tricuspid septum control points, 28 tricuspid valve control points, and 18 pulmonary valve control points) and four surface geometries (RV apex, RV output tract, and RV inflow tract). The right atrial surface 206 is constrained by 28 tricuspid valve control points and links to the right ventricle 204.

FIG. 2C shows a model for the aortic valve 208. The aortic valve model 208 is constructed from 11 landmarks (3 commissures, 3 hinges, 3 leaflet tips, and 2 ostias) and four surface structures (aortic root, N-leaflet, L-leaflet, and R-leaflet). The aortic root is constrained by the hinge and the commissure plane, and each leaflet spans between two commissures and one hinge.

FIG. 2D shows a model for the mitral valve 210. The mitral valve model 210 is constructed from seven landmarks (3 trigones, 2 commissures, and 2 leaflet tips). The anterior leaflet is defined by two trigones, one leaflet tip, and two commissures, and the posterior leaflet is defined by three trigones, one leaflet tip, and one commissure.

FIG. 2E shows a model of the pulmonary valve 212. The pulmonary valve model 212 is constructed from nine landmarks (3 commissures, 3 hinges, and 3 leaflet tips) and four surface structures (pulmonary root, N-leaflet, L-leaflet, and R-leaflet).

FIG. 2F shows a model of the tricuspid valve 214. The tricuspid valve model 214 is constructed from four surface geometries (annulus, septal leaflet, anterior leaflet, and posterior leaflet) and six anatomical landmarks (three commissures and three leaflet tips).

Figure 3:
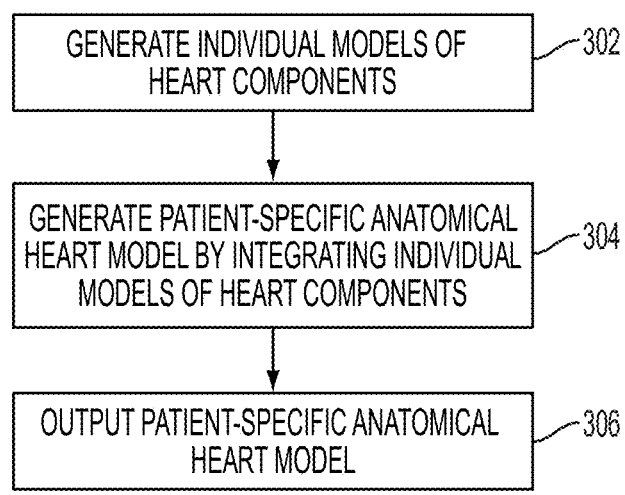
FIG. 3 illustrates a method for generating a patient-specific 4D anatomical model of the heart according to an embodiment of the present invention.

The patient-specific 4D anatomical model gives the morphology of the patient's heart and can be used to determine morphological (dimensions) and dynamic parameters for any component of the heart. FIG. 3 illustrates a method for generating a patient-specific 4D anatomical model of the heart according to an embodiment of the present invention. The method of FIG. 3 transforms image data representing a coronary region of a patient to generate a patient-specific anatomical model of the heart for that patient. The method of FIG. 3 can be used to implement step 104 of the method of FIG. 1. The method of FIG. 3 for generating the patient-specific anatomical model of the heart is described in greater detail in United States Published Patent Application Nos. 2010/0280352 and 2011/0060576, the disclosures of which are incorporated herein by reference.

At step 302, an individual model is generated from the received image data for each of a plurality of heart components. According to an embodiment of the present invention, models are generated for the heart chambers: left ventricle (LV) (endocardium and epicardium), right ventricle (RV), left atrium (LA) and right atrium (RA); valves: mitral valve, aortic valve, pulmonary valve, and tricuspid valve; and main vessels: aorta and pulmonary trunk. All of these portions of the heart are referred to herein collectively as the "heart components". For each heart component, a physiological model of the heart component is estimated in each frame of the 4D image data using a discriminative database-guide estimation/detection technique.

The physiological model of each anatomic structure (heart component) is constructed offline prior to generating the personalized heart model for a particular patient. Each physiological model is generated based on a mathematical representation of the corresponding heart component in a set of annotated training data. For example, the physiological model for each heart component can be generated using mean shapes of the heart component in a set of annotated training data. For example, United States Patent Application Publication No. 2008/0101676, which is incorporated herein by reference, describes a generating a four-chamber physiological heart model and fitting the heart model to image data. As described therein, the heart model is a 3D mesh and initial meshes for each chamber are generated using mean shapes of the chambers in annotated training data. Further, United States Patent Application No. 2009/0123050, which is incorporated herein by reference, describes a 4D physiological model of the aortic valve. A physiological model can similarly be generated offline for each of the heart components based on a set of annotated training data.

In order to estimate a physiological model of a particular heart component in a 3D image (i.e., frame of a 4D image sequence), the parameters of the physiological model are estimated to fit the image using a discriminative machine-learning technique based on a large database of annotated training images. According to one embodiment, marginal space learning (MSL) is used to localize the physiological model in each of the images.

The idea of MSL is not to learn a classifier directly in a full similarity transformation parameter space, but to incrementally learn discriminative classifiers in increasing dimensionality based on annotated training data. As the dimensionality increases, the valid (positive) space region becomes more restricted by previous marginal space classifiers. In order to estimate a physiological model of an anatomic structure, such as a particular heart component, in an image, the estimation of the similarity transformation (i.e., position, orientation, and scale) corresponding to the location of the heart component can be split into three stages: position estimation, position-orientation estimation, and full similarity transformation estimation. A discriminative classifier is trained for each stage based on the training data. All of the discriminative classifiers can be trained as Probabilistic Boosting Trees (PBTs). In addition to reducing the size of the search space, another advantage of MSL is that it is possible to use different features, such as 3D Haar features or steerable features to train the classifier in each marginal space level.

Examples of estimating physiological models of various heart components in 3D image data using MSL are described in the following publications, the disclosures of which are incorporated herein by reference: United States Patent Application Publication No. 2008/0101676, describes estimating a model for each chamber of the in 3D CT image data; United States Patent Application No. 2009/0123050, describes fitting a physiological model of the aortic valve to 4D CT data; and Yang et al., "3D Ultrasound Tracking of the Left Ventricles Using One-Step Forward Prediction and Data Fusion of Collaborative Trackers", CVPR 2008, describes fitting a model of the left ventricle to a sequence of 3D ultrasound images. It is to be understood that each of the heart components can be estimated by fitting a physiological model of the heart component to image data using discriminative machine-learning techniques, similarly to the above examples.

Once the parameters of each individual heart component model are estimated in each frame of the 4D image data, e.g., using MSL, learning-based boundary detection can be performed on the individual heart component model in each image to refine the estimated model parameters. In particular, the boundary of each estimated model can be refined using the learning-based boundary detection to increase the accuracy of the physiological model estimation for each heart component.

At step 304, the patient-specific 4D personalized anatomical model of the heart is generated by integrating the individual models generated for each of the heart components.

Each of the individual heart component models resulting from step 402 is a mesh made of a certain number of points. According to an advantageous implementation, in order to integrate the individual models of the LV (endocardium and epicardium), RV, LA, RA, mitral valve, aortic valve, aorta, and pulmonary trunk, mesh point correspondences are established between connecting or overlapping models. The mesh point correspondences allow the models to be correctly aligned with respect to each other. It is possible to establish mesh point correspondence between models by re-sampling the models. For example, United States Patent Application Publication No. 2008/0262814, which is incorporated herein by reference, describes various re-sampling methods to establish mesh point correspondence between models of the four heart chambers in order to correctly align the heart chamber models. It is to be understood that the techniques described in United States Patent Application Publication No. 2008/0262814 can be extended to establish mesh point correspondence between the individual heart component models described herein.

At step 306, the patient-specific 4D anatomical heart model is output. The patient-specific 4D anatomical heart model can be output by storing the patient-specific 4D anatomical heart model to a memory, storage, or computer readable medium. The patient-specific 4D anatomical heart model can also be output by displaying the patient-specific 4D anatomical heart model or printing an image of the patient-specific 4D anatomical heart model. The output patient-specific 4D anatomical heart model can be used for further medical image processing. For example, the 4D personalized anatomical heart model can be used to estimate various morphological and functional measurements of the heart. The 4D personalized anatomic heart model can also be used to simulate blood flow or blood-tissue interaction, as described in the subsequent steps of the method of FIG. 1.

As described above, the method of FIG. 3 illustrates a method for generating the patient-specific 4D anatomical model according to one embodiment. In another embodiment, the parameters of the 4D anatomical model may be estimated for a patient following a coarse to fine strategy based on the natural level of detail of the underlying anatomies. In a first step, the pose and corresponding motion parameters of each model component are recovered from the received 4D image data using a method that combines MSL with random sample consensus (RANSAC) techniques to obtain robust and time-coherent object localization. This method is described in detail in Ionasec et al., "Patient-Specific Modeling and Quantification of the Aortic and Mitral Valves from 4D Cardiac CT and TEE", *IEEE Transactions on Medical Imaging*, 2010, which is incorporated herein by reference. In a second step, the anatomical landmarks' locations and motion are simultaneously estimated using a trajectory spectrum learning (TSL) algorithm, which employs trajectory-based features and strong trajectory spectrum classifiers. The TSL algorithm is described in greater detail in Ionasec et al., "Robust Motion Estimation Using Trajectory Spectrum Learning: Application to Aortic and Mitral Valve Modeling from 4D TEE", *Proceedings of 12th IEEE International Conference on Computer Vision,* 2008, pages 1601-1608, which is incorporated herein by reference. In the final step, boundary delineation of the complete heart surfaces is performed over the entire cardiac cycle. This method leverages robust boundary detectors together with collaborative trackers and motion manifolds.

Figure 4:
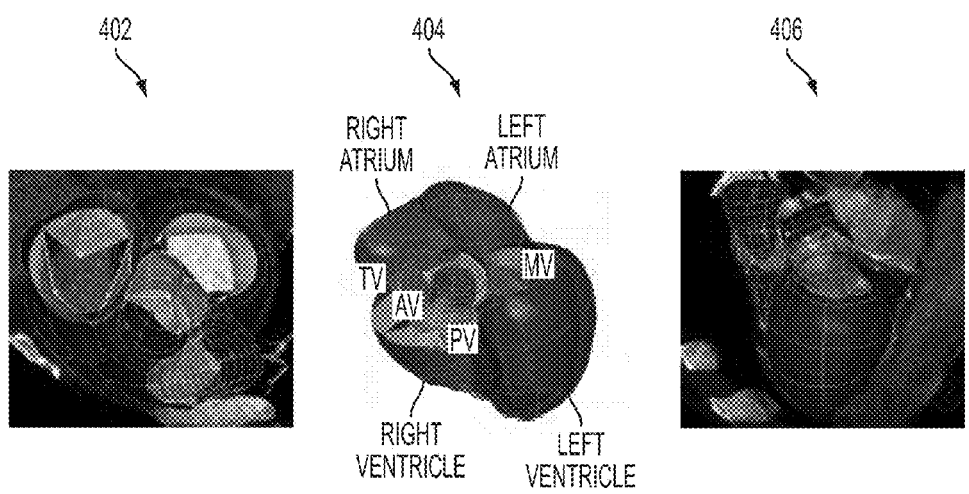
FIG. 4 illustrates an exemplary patient-specific anatomical heart model estimated from a multiphase CT sequence.

FIG. 4 illustrates an exemplary patient-specific anatomical heart model estimated from a multiphase CT sequence. As illustrated in FIG. 4, images 402, 404, and 406 show the left ventricle, left atrium, right ventricle, right atrium, aortic valve (AV), mitral valve (MV), pulmonary valve (PV), and tricuspid valve (TV), as well as the ascending aorta and pulmonary artery. Although FIG. 4 does not show the entire aorta, it is to be understood that the aorta may also be estimated as part of the patient specific 4D anatomical model. For example, the aorta can be estimated using the method described in United States Published Patent Application No. 2010/0239148, the disclosure of which is incorporated herein by reference.

Returning the FIG. 1, at step 106, blood flow (hemodynamics) in the heart is simulated based on the patient-specific 4D anatomical model. In order to simulate the blood flow, the patient specific geometry serves as an input to a 3D Navier-Stokes solver that derives realistic hemodynamics, constrained by the local anatomy, along the entire heart cycle.

The hemodynamics calculations described herein us a classical continuum model for the blood. The incompressible Navier-Stokes equations with viscous terms (Equation (1) below), which are the standard continuum mechanics model for fluid flow, are solved using Direct Numerical Simulation in a level set formulation:

$$\rho\left(\frac{\partial u}{\partial t} + u \cdot \nabla u\right) = -\nabla p + \mu \Delta u + F \quad (1)$$

$$\nabla \cdot u = 0$$

Navier-Stokes are partial differential equations describing the momentum and mass conservation for fluid flow, depending on the velocity u and pressure p of the fluid, as well as the fluid density $\rho$ and dynamic viscosity $\mu$. The blood density and dynamic viscosity can be set to generic mean values across healthy individuals, namely $\rho=1.05$ g/cm$^3$ and $\mu=4$ mPa·s. F represents other body forces acting on the fluid. The equations are solved using numerical discretization on a uniform grid, employing both finite difference and finite volume techniques. In particular, embodiments of the present invention utilize the fractional step combined with an approximate projection for the pressure.

According to an advantageous implementation, the blood is modeled as a Newtonian liquid. Previous numerical studies have found that, in larger arteries, the non-Newtonian behavior of the blood is not important during most of the cardiac cycle. The non-Newtonian importance factor (defined as the ratio of the non-Newtonian and the Newtonian viscosity of blood) becomes significant during a 15-20% subperiod of the cardiac cycle, achieving a peak during a speed deceleration period when velocity is close to zero. Blood dynamics in the heart is mostly governed by high velocities, or rather, high shear rates. This, combined with the fact that blood's rheology is close to that of a Bingham plastic liquid (a material that behaves as a rigid body at low stresses but flows as a viscous fluid at high stress), supports the qualitative conclusion that during the heart cycle, blood's dynamics is predominantly Newtonian. The likely exceptions are: timewise the diastasis, and spacewise the apical and jet stagnation regions.

Computing fluid dynamics in moving generic geometries and/or involving multiphase flow constitutes a challenge, especially when it comes to devising computational methods that are simple and robust, as well as accurate. Level set methods have achieved some success in dealing with such complex computations, being able to capture the intricate dynamics of interfaces between different materials (for example, water and air, or a complex deforming object and a liquid). The Navier-Stokes equations are cast into a form that takes into account such a description. For example, for two fluids with different density and viscosity, the level set formulation of the Navier-Stokes equations can be expressed as:

$$\rho(\varphi)\left(\frac{\partial u}{\partial t} + u \cdot \nabla u\right) = -\nabla p + \mu(\varphi)\Delta u + F \quad (2)$$

$$\nabla \cdot u = 0$$

$$\rho(\varphi) = \rho^1(\varphi)H(\varphi) + \rho^2(\varphi)(1 - H(\varphi))$$

$$\mu(\varphi) = \mu^1(\varphi)H(\varphi) + \mu^2(\varphi)(1 - H(\varphi))$$

$$H(\varphi) = \begin{cases} 1, & \varphi > 0 \\ 0, & \varphi < 0 \end{cases}$$

In Equation (2), H is the Heaviside function used to create a numerically sharp distinction between the first fluid, characterized by positive values of the level set $\varphi$, and the second fluid, characterized by negative values of the level set $\varphi$. The level set formulation, especially when implemented using advanced methods such as the ghost fluid method, has several advantages over classical formulation. For example, advantages of the level set formulation include ease of computations of free surface flow and deforming materials interacting with fluids, simple implementations for tensor extrapolation technologies, and simple formulas for various geometric parameters, such as normal fields ($\vec{n}=\nabla\varphi/|\nabla\varphi|$) or mean curvature fields (e.g., k=$\Delta\varphi$ for level set function of unit gradient).

Another important advantage of describing the heart dynamics in the level set framework is the possibility of automatically dealing with moving/heavily deforming walls without the need to generate a new computational grid at every several time steps, when the previous grid becomes too skewed to robustly handle the numerical calculations, as is the case in Finite Element Models (FEM). This allows for automatic integration of the patient-specific cardiac meshes into the blood flow simulation engine, and offers a framework for clinical usage of cardiac models for obtaining patient-specific hemodynamics.

Figure 5:
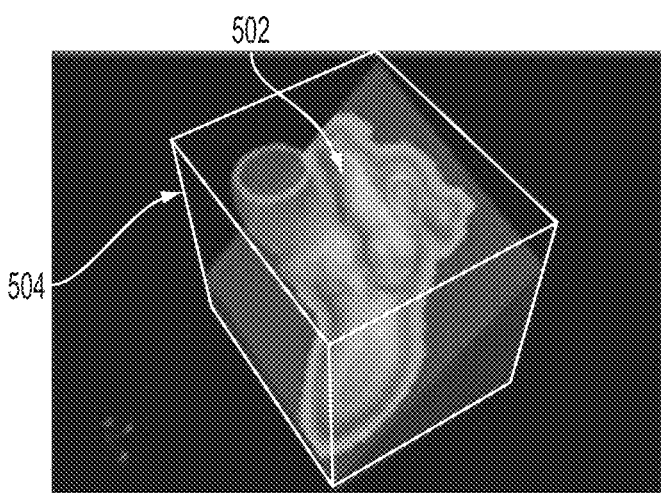
FIG. 5 illustrates a patient-specific anatomic heart model embedded as a level set in a rectangular domain.

According to an advantageous embodiment of the present invention, the heart walls/blood interface are modeled using a level set. More precisely, a heart mesh sequence having a certain number of frames (e.g., 10 frames), obtained as described above in step 104, is interpolated using splines to derive the mesh at a given simulation time. This mesh is embedded in the computational domain with the help of the level set function $\varphi$, defined as $\varphi(x)=\text{dist}(x,\text{mesh})-dx$, where dx is the grid spacing. The heart/blood interface as used in the code is defined as the zero level of the level set function, effectively "thickening" the original triangle mesh by dx on each side. FIG. 5 illustrates a patient-specific anatomic heart model 502 embedded as a level set in a rectangular domain 504. FIG. 5 shows the transparent zero level corresponding to the thickened heart walls.

The interface location is used to impose no-slip boundary conditions to the fluid region. The mesh velocity at each time step is easily computed by temporal interpolation from the mesh positions at adjacent time steps, then extrapolated using extrapolation kernels. Note that imposing boundary conditions in this manner effectively enforces one-way transfer of momentum from the solid heart mesh to the fluid. This approach essentially models the heart as a pump pushing against the domain walls, which can approximate the resistance of the circulatory system.

Figure 6:
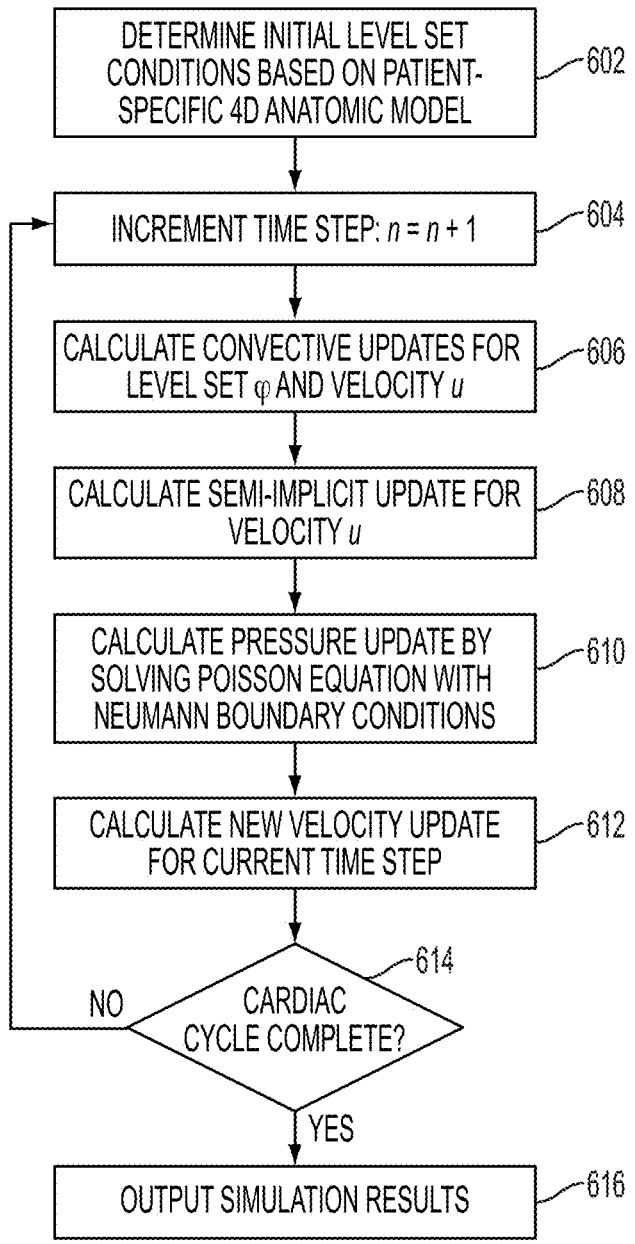
FIG. 6 illustrates a method of simulating blood flow in the heart based on a patient-specific anatomical heart model according to an embodiment of the present invention.

FIG. 6 illustrates a method of simulating blood flow in the heart based on a patient-specific anatomical heart model according to an embodiment of the present invention. The method of FIG. 6 can be used to implement step 106 of FIG. 1. The method of FIG. 6 described in detail the solution of the Navier-Stokes equations (2) in the level set framework. The method of FIG. 6 can be used to solve all stages of the cardiac cycle, including the isovolumetric phases (IP). It can be noted that the IP are not periods of stasis, but rather phases with dynamic changes in the intracavitary flow. The method of FIG. 6 can be used to simulate blood flow in the whole heart anatomy or in one or more heart components. In the description of FIG. 6, At step 602, initial level set conditions are determined at an initial time (n=0) based on the location of the patient specific heart model (i.e., the mesh) at the initial time. The determination of the zero level of the level set function $\varphi$ and the velocity u is described above. The initial pressure p can be determined by solving the Poisson equation with Neumann boundary conditions imposed based on the mesh location.

At step 604, the time step n from the level set is incremented, such that n=n+1. At step 606, convective updates for the level set $\varphi$ and the velocity u are calculated. In this step, the level set values are updated using the mesh location at the given time step. In an intermediate geometric step, connected components defined by the new level set are calculated. This is used subsequently for robust connected component-by-component inversion of the implicit viscous and pressure Poisson linear systems. The convective force terms are then calculated using third order accurate ENO (Essentially Non-Oscillatory) techniques.

At step 608, the velocity is semi-implicitly updated to take into account the viscous force contribution. In particular, the velocity is updated to u* using second-order semi-implicit splitting, and by inverting the system using an efficient multigrid preconditioned conjugate gradient solver.

At step 610, the pressure is updated by solving the Poisson equation with Neumann force boundary conditions. The Poisson equation is also solved in each of the connected components of the discretization domain by inverting the system using an efficient multi-grid preconditioned conjugate gradient solver. Before the system inversion, the velocity is overwritten in the solid regions using the solid velocity.

At step 612, a new velocity update at the current time step is calculated. In particular, the density is updated using the new level set, and the velocity update is calculated as $u^n=u^*-\nabla p^n/\rho^n$ in the liquid, or $u^n=u^{solid}$ in the solid. The interface location is used to impose no-slip boundary conditions to the fluid region in, namely $u^{fluid}=u^{solid}$ in for the convective (step 606) and viscous (step 608) components of the Navier-Stokes momentum equation, and $\partial p/\partial n=(u^*-u^{solid})\cdot\vec{n}$ for the pressure Poisson equation (step 610). Here, $\vec{n}$ is the normal vector field, calculated from the level set as described above. The global accuracy of the method is second order in the interior of the domain, and this drops to first order at the boundaries.

At step 614, it is determined if the simulation has been completed for the entire heart cycle. If this simulation has not yet been completed for the entire heart cycle, the method returns to step 604 and increments another time step. Steps 606-612 are then performed again for the next time step. If the simulation has been completed for the entire heart cycle, the method proceeds to step 616. At step 616, the simulation results are output.

The human heart functions as part of the cardiac system, thus being influenced by the loading pressures from the venous and arterial systems. The above described simulation framework solves the Navier-Stokes equations with prescribed (wall) boundary motion, thus ensuring that it is not necessary to calculate the pressure field, but instead its gradient can be calculated, as the pressure is a relative rather than absolute variable. In other words, the first Navier-Stokes equation in (2) (momentum conservation) is invariant to gauge shifts of the pressure, as long as its gradient does not change. Mathematically, the pressure Poisson equation with Neumann boundary conditions has a one-parameter family of solutions, which can be fixed once a Dirichlet boundary condition is introduced. Therefore, when solving the pressure Poisson equations, the solution can be fixed by selecting a base pressure (equal to zero) at a point outside the aorta, and this acts in a similar way as imposing p=0 at the aortic outflow surface.

As a note, any value can be selected for the base pressure, for example, using the values from a generic physiological curve, and this does not influence the hemodynamics in the prescribed motion framework presented above. This, however, would influence the dynamics in the FSI problems described below, where deformable tissues respond to the pressure boundary value changes, or in the case of double regurgitations, where both the aortic and the mitral valves (or their right side homologues) are leaking. For such cases, it is necessary to couple the model with a one dimensional vascular model.

Figure 7:
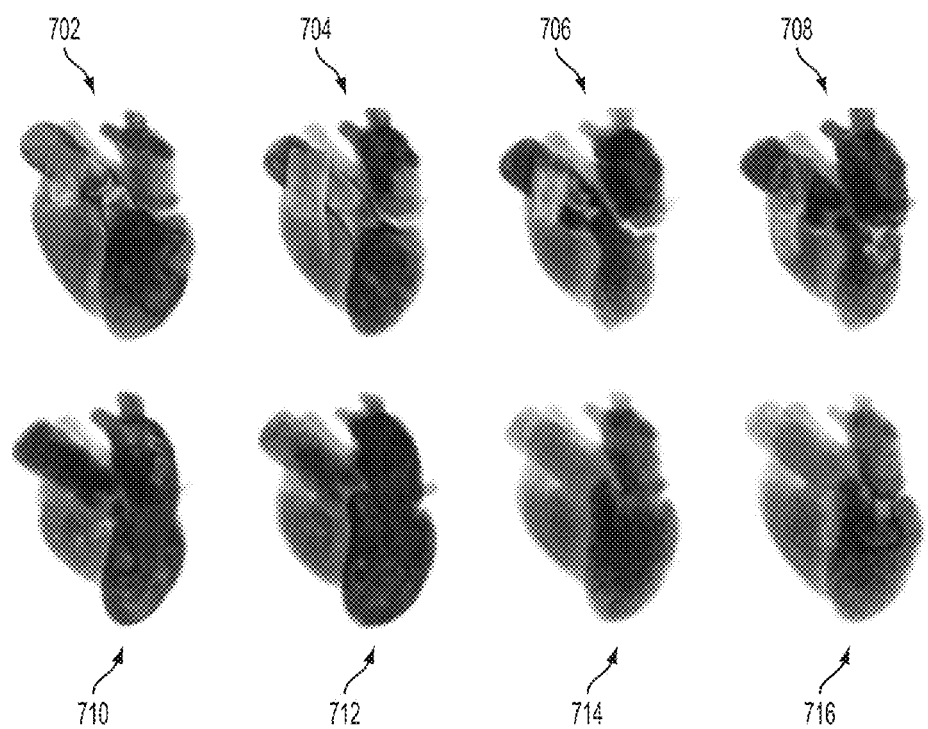
FIG. 7 illustrates exemplary blood flow simulation results using the method of FIG. 6.

FIG. 7 illustrates exemplary blood flow simulation results using the method of FIG. 6. The images 702-716 of FIG. 7 were generated using a series of blood flow simulations using a patient-specific anatomic heart model. In this example, the left and right sides were not connected through the systemic circulation, due to lack of geometric and material data for a full vessel tree. Consequently, the simulations were performed separately for each side of the heart, which may be more computationally efficient, and is not influenced by the slightly different stroke volumes in the left and right side of the heart model. Images 702-716 of FIG. 7 show vorticity magnitude for the left and right heart blood flow in the beginning systole 702, mid systole 704, late systole 706, beginning diastole 708 (showing pulmonary valve regurgitation), early diastole 710, mid-diastole 712, diastasis 714, and late mitral filling 716 stages of the heart cycle.

Returning to FIG. 1, at step 108, fluid structure interactions are estimated based on the simulated blood flow. Fluid structure interaction can be used in conjunction with the hemodynamics simulation (step 106) to simulate the deformation of heart components in the patient specific 4D model. In particular, the framework described above in step 106 for hemodynamic simulation can be coupled with a model for a particular structure's biomechanics. Each heart component can be modeled as a passive tissue whose motion is governed by a constitutive law. A Finite Element Model (FEM) may be used to solve the partial differential equations related to that law. The wall motion of a particular structure (e.g., the aorta) is driven by two forces:

1. An internal force that models the passive properties of the tissue. For example, it is possible to model a structure, such as the aorta, by a linear, isotropic, mono-layer elasticity model with co-rotational correction to cope with large deformations. It is also possible to utilize a more detailed model to simulate the heterogeneous composition of the artery (anisotropy, three main layers (tunica intima, tunica medica, and tunica adventitia), non-linearity, etc.).
2. An external force that models the loading generated by blood flow inside the structure. That loading, which translates into pressures, is applied to the inner layer of the structure.

Figure 8:
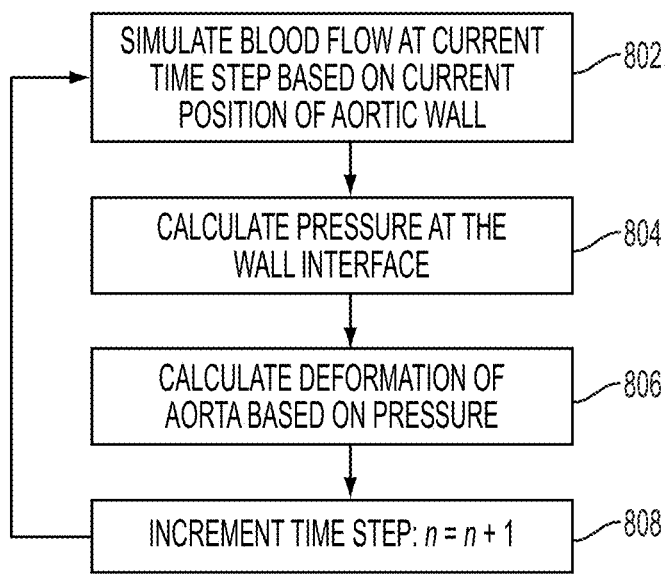
FIG. 8 illustrates an iterative method for estimating fluid structure interaction (FSI) of the aorta according to an embodiment of the present invention.

FIG. 8 illustrates an iterative method for estimating fluid structure interaction (FSI) of the aorta according to an embodiment of the present invention. It is to be understood that a similar method may be applied to other components of the heart model to estimate fluid structure interactions. At step 802, the blood flow is simulated at a given time step based on a current position of the aortic wall. The blood flow can be simulated based on the position of the aortic wall in the in the patient-specific 4D anatomical model at the current time step using the method of FIG. 6 described above. At step 804, the pressure at the wall interface is calculated at the current time step. It can be noted that the pressure at the blood/structure interface is calculated at each time step in the method of FIG. 6. At step 806, a deformation is calculated for the aorta based on the pressure at the wall interface. The pressure acts as an external force on the wall of the aorta and causes the aorta to deform based on wall motion forces modeled for the aorta. At step 808, the time step increments (n=n+1), and the method returns to step 802. Accordingly, the calculated deformation of the aorta is used to simulate blood flow at the next time step. The method repeats until the end of the simulation. For example, the method may be repeated until a full heart cycle is simulated.

Figure 9:
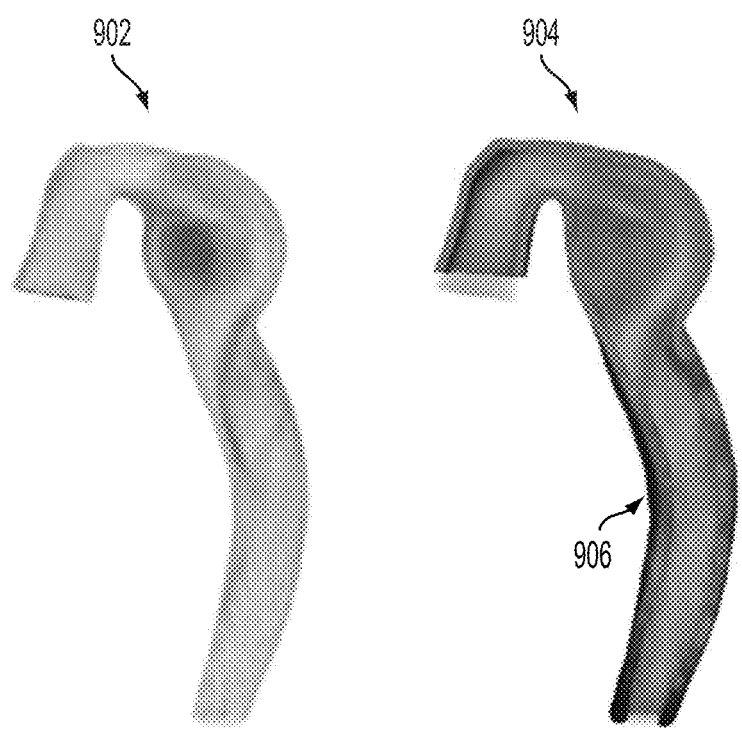
FIG. 9 illustrates exemplary results of estimating fluid structure interactions for the aorta.

FIG. 9 illustrates exemplary results of estimating fluid structure interactions for the aorta. Image 902 shows the blood flow simulation in the aorta at a particular time step. Image 904 shows the fluid structure interaction based on the blood flow simulation of image 904, which results in a deformed aortic wall 906.

The FSI simulation can be used to estimate intrinsic properties of a structure, such as tissue stiffness by coupling the above described FSI framework with inverse problem strategies (e.g., Kalman filtering or trust-region techniques). In this way, the model parameters for the motion of the structure can be adjusted such that the simulated motion of the parameter in the FSI simulation matches the motion observed in the medical images. One possible implementation is to minimize a cost function that evaluates how much the simulated motion differs from the observation. This can result in an estimated biomechanical parameter for the structure, such as wall stiffness. A method for implementing fluid structure interaction and estimating a biomechanical parameter of the aorta is described in detail in United States Published Patent Application No. 2011/0060576, which is incorporated herein by reference.

Figure 10:
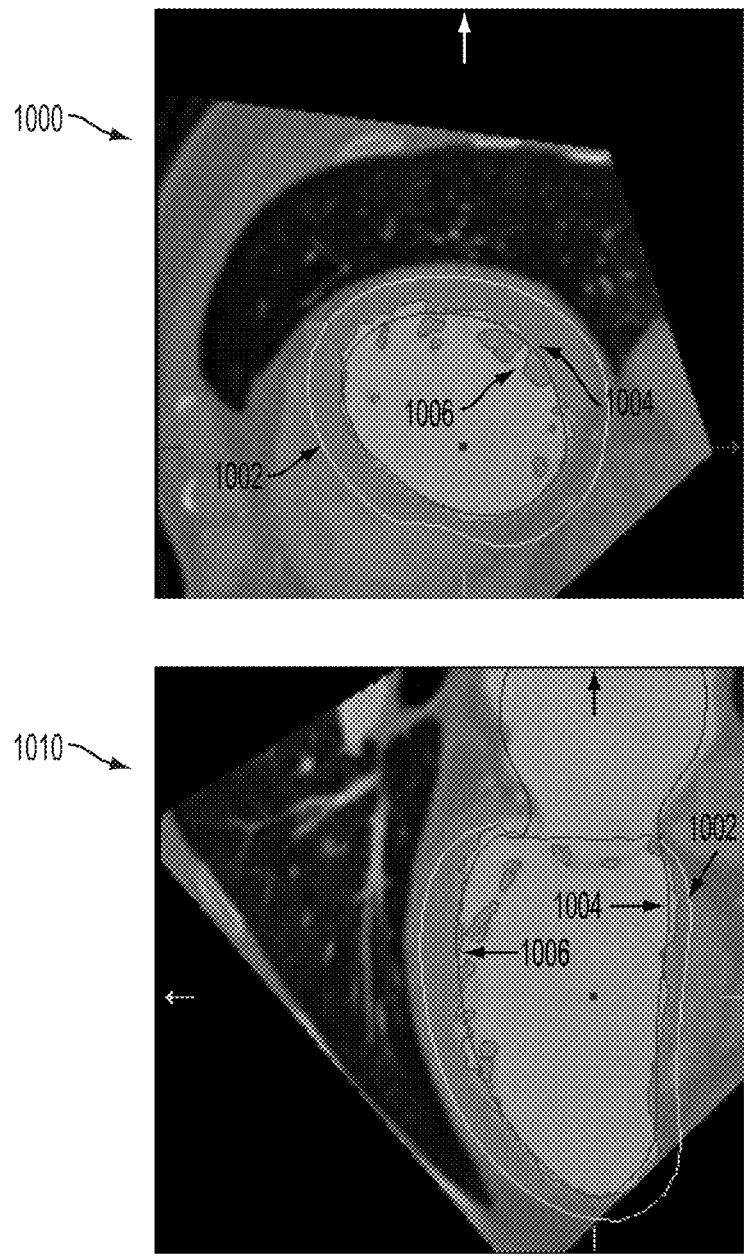
FIG. 10 illustrates a multi-scale anatomical model of the LV

As described above, the patient-specific anatomical models for the various heart components are smooth meshes, and the hemodynamics simulation and the fluid structure interaction are performed based on the smooth meshes of the heart components. According to an advantageous embodiment of the present invention, the patient-specific anatomical model may be implemented as a multi-scale anatomical model in which the smooth heart model described above is at a coarser scale and a more detailed anatomical model exists at a finer scale. For example, the patient specific anatomical model of the LV may be used to extract a model of the LV endocardium at a finer resolution that includes the papillary muscles and the trabecule. FIG. 10 illustrates a multi-scale anatomical model of the LV. As shown in images 1000 and 1010 of FIG. 10, the multi-scale anatomical model of the LV includes the LV epicardium 1002, a coarse scale LV endocardium 1004, and a fine scale LV endocardium 1006, which includes the papillary muscles and the trabecule. A method for extracting such a multi-scale LV model is described in detail in United States Published Patent Application No. 2009/0080745, which is incorporated herein by reference. The hemodynamic simulation (step 106) can be constrained based on the location of the fine scale anatomical model for one or more of the heart components. In addition, the fluid structure interaction (step 108) can be estimated based on the fine scale anatomical model for one or more of the heart components.

Returning to FIG. 1, at step 110, the comprehensive modeling results are output. For example, the resulting patient-specific 4D anatomical model, blood flow simulations, and/or fluid structure interaction simulations can be output by displaying images representing such results. Further, the comprehensive modeling described in steps 104, 106, and 108 result in anatomic and morphological parameters (step 104), hemodynamic parameters (step 106), and biomechanical parameters (step 108) that give a comprehensive view of a patient's heart function. These parameters can be stored, for example, in a memory or storage of a computer system or on a computer readable medium. These parameters (or models) can also be used for further evaluation of the patient, for example in steps 112 and 114, described below.

At step 112, non-invasive assessment and diagnosis of the patient's heart can be performed using the comprehensive modeling results. The modeling of steps 104, 106, and 108 gives a comprehensive view of the current state of the patient's heart. This can be used for assessing the current structure or hemodynamics of a patient's heart, to assess a previously diagnosed heart disease, or for non-invasive diagnosis of heart problems.

According to an embodiment of the present invention, the comprehensive patient specific heart model can be used for precise quantification of the anatomy and function of the heart. The clinical gold standard still processes 2D images and performs manual measurements which are tedious to obtain and may be inaccurate. The present inventors propose a paradigm shift in the clinical evaluation of the heart, in which manual analysis based on 2D images is replaced with automated model-based quantification from 4D data. Various examples of clinical measurements that can be extracted automatically are described below.

Figure 11:
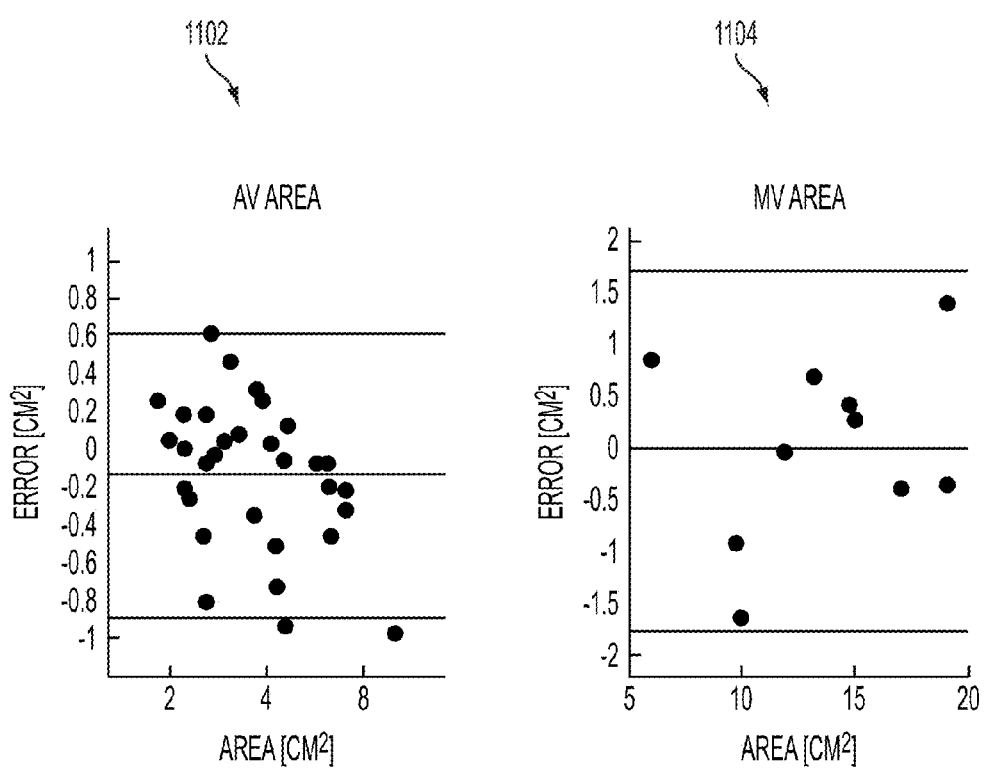
FIG. 11 illustrates the precision of the measurements for the aortic valve area and the mitral valve area.

Table 1 shows the measurement results for various dimensions of the aortic-mitral coupling measured from patient-specific 4D anatomical models including diameters of the ventricular-arterial junction (VAJ), sinus of valsalva (SV) and sinotubular junction (SJ), mitral annular circumference (AC), anteroposterior diameter (APD), and anterolateral-posteromedial diameter (AL-PM-D). FIG. 11 illustrates the precision of the measurements for the aortic valve area (AV area) and the mitral valve area (MV area). In particular, FIG. 11 shows Bland-Altman plots for the AV area 1102 and the MV area 1104. The aortic valve experiments were performed on CT data from 36 patients and the mitral valve was evaluated on tee data from 10 patients.

TABLE 1

|  | Mean | STD |
| --- | --- | --- |
| VAJ (cm) | 0.137 | 0.017 |
| SV (cm) | 0.166 | 0.043 |
| STJ (cm) | 0.098 | 0.029 |
| AC (cm) | 0.846 | 0.3 |
| APD (cm) | 0.325 | 0.219 |
| AL-PM-D (cm) | 0.509 | 0.37 |

The motion pattern of a chamber during a cardiac cycle provides many important clinical measurements of its functionality, such as, the ventricular ejection fraction, myocardium wall thickness, and dissynchrony within a chamber or between different chambers. Some benefits of the model-based analysis include precision, efficiency, and comprehensiveness.

Another possible application for the compressive patient-specific 4D model is for automated diagnosis and case retrieval. Clinical decisions are largely based on generic information and rule sets from clinical guidelines and publications, and personal experience from clinicians. In addition to the quantitative qualities discussed above, the comprehensive cardiac model can be used to automatically derive high-level clinical information using learning-based discriminative distance functions. An inference can be formulated in a comprehensive feature space, which incorporates the complex morphological and functional information. In exemplary implementations, this is used to perform two general tasks: retrieval of similar cases using a learned distance function, which measures the similarity of two particular cardiac shapes; and a binary classification problem based on geometric models and derived features.

For distance learning two techniques, namely learning from equivalence constraints and the intrinsic Random Forest distance, are discussed herein, but the present invention is not limited thereto. Equivalence constraints are represented using triplets of two model instances' feature vectors and a label indicating whether the two instances are similar or dissimilar. Learning from these triplets is often called learning in the product space and demonstrated to be effective for high dimensional data with many correlated, weekly relevant and irrelevant features. The signed margin of models constructed using boosting or Random Forests can be used as the required distance function.

Figure 12:
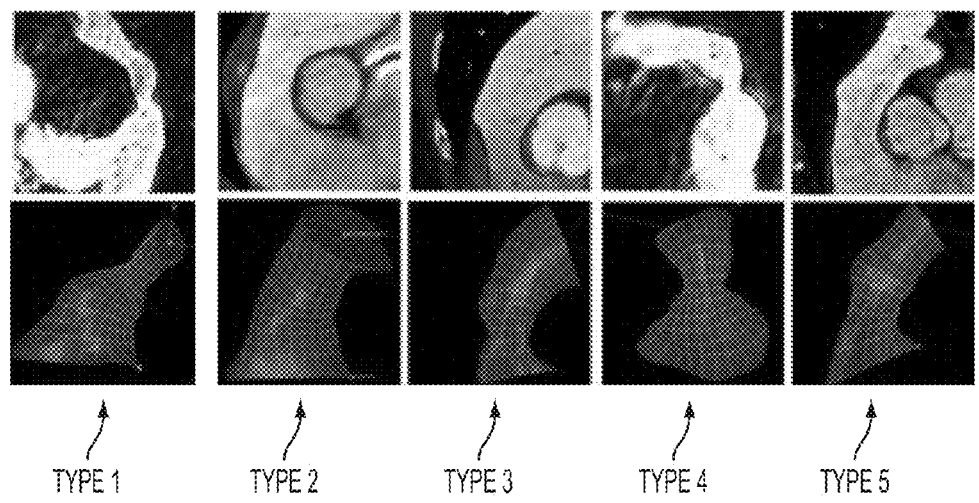
FIG. 12 illustrates various types of pulmonary trunk morphologies.

The generic approach enables learning arbitrary user-defined concepts of similarity depending on the application. This is demonstrated with two exemplary applications: 1) diagnosis and severity assessment of aortic valves; and 2) patient selection for Percutaneous Pulmonary Valve Implantation (PPVI). Regarding patient selection for PPVI, the morphology of the pulmonary trunk is a major determinant for a patient's suitability for PPVI. Intervention in unsuitable patients exposes them to unnecessary invasive catheterization. FIG. 12 illustrates various types of pulmonary trunk morphologies. As shown in FIG. 12, type 1 is pyramidal shaped, type 2 is constant diameter, type 3 is inverted pyramidal shaped, type 4 is narrowed centrally but wide proximally and distally, and type 5 is wide centrally but narrowed proximally and distally. Patients from type 1 are considered to be unsuitable for PPVI due to the narrow artery and high probability of device migration. Accordingly, shape features extracted from the estimated pulmonary trunk, which can be estimated as part of the patient-patient specific anatomical model, can be used to learn a discriminative distance function to discriminate anatomies of type 1 from other classes in order to automatically determine whether a patient is suitable for PPVI.

In addition to the patient-specific anatomical heart model, the patient-specific hemodynamics of the heart can also be used for non-invasive assessment and diagnosis as well. In particular, the hemodynamics of cardiac cycle events can be simulated, as described above in step 106 of FIG. 1. An exemplary simulation of cardiac cycle events is described herein. The simulation domain was discretized using a $128^3$ regular grid, which corresponds to a physical resolution of 1 mm, while the time step was 0.001 seconds. To ensure stability, subcycling was used whenever the maximum velocity would be greater than dx/0.001, i.e., the Courant-Friedrichs-Lewy (CFL) number max(u)*0.001/dx became greater than 1. The heart bounding box occupied 95% of the domain.

Figure 13:
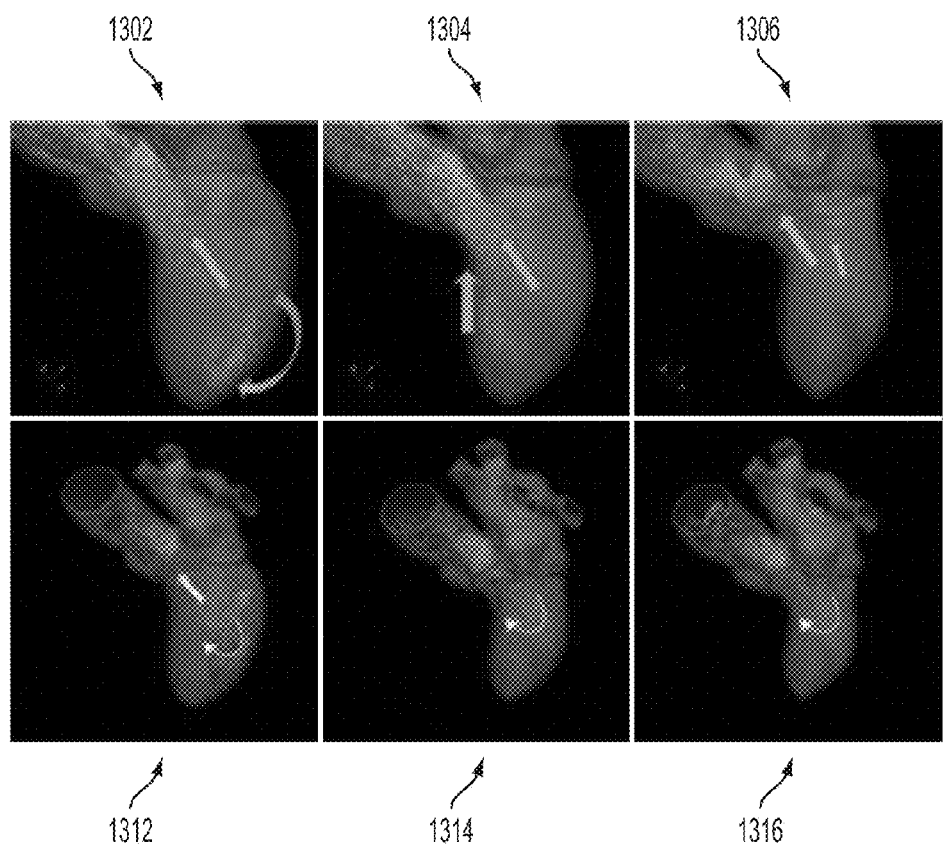
FIG. 13 illustrates hemodynamics simulations of systolic events and structures.

FIG. 13 illustrates hemodynamics simulations of systolic events and structures. As shown in FIG. 13, images 1302, 1304, and 1306 show simulated blood flow velocity in the heart in early systole, mid-systole, and end-systole phases, respectively. Images 1312, 1314, and 1316 show vorticity isosurfaces generated based on the simulated velocities in the early systole, mid-systole, and end-systole phases, respectively. The particular heart for which the simulation has been performed has a systole of 290 ms in a cardiac cycle of 925 ms. As shown in images 1302 and 1312, the initial flow conditions inherited from the diastole and the isovolumic contraction (IVC) phases have remnants of the toroidal vortex from the late mitral filling. This feature dominates the lower ventricular pattern in the early systole (ES), such that the apical blood pool is mostly recirculated by the vortex. Interestingly, the initial conditions also feature a counter clockwise rotation, as seen from the apex, which reverses into a clockwise rotation during the systole.

As shown in images 1304 and 1314, the mid-systole features a strong aortic flux, often with vortical strands aligned with the aortic axis, which guides the right-handed helix motion of the blood into the aorta. This counterclockwise rotation of the blood continues downstream in the lower ascending aorta, and is a well known feature of a healthy aortic flow. These computational results are based on meshes obtained from CT data, and hence do not include torsional motion. They support a conclusion that the aortic right-handed helical rotation is mainly determined by the geometric disposition of the aortic longitudinal axis with respect to the aortic valve base plane and the aortic valve geometry itself, rather than the LV torsional motion. As shown in images 1306 and 1316, in end-systole, the vortical strand is weaker and the fluid particles entering the aorta define wider spiraling paths.

The flux is strong as well in the right heart's early and mid-systole, with similar features as described above, however, a regurgitant flux is visible at the end of the systolic phase due to a regurgitating pulmonary valve.

Figure 14:
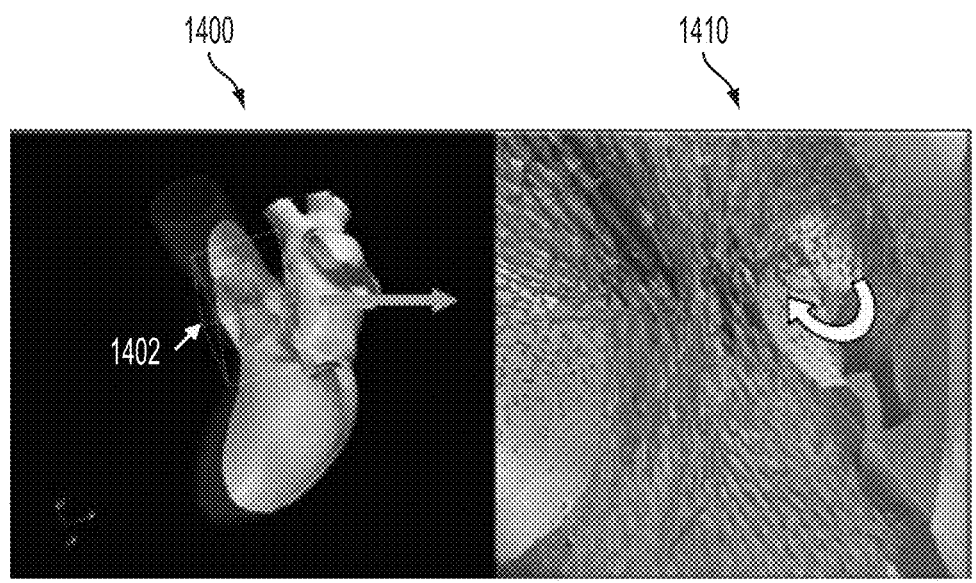
FIG. 14 illustrates the formation of vortices in an aortic valve sinus region obtained using blood flow simulation.

FIG. 14 illustrates the formation of vortices in an aortic valve sinus region obtained using the blood flow simulation. As illustrated in FIG. 14, image 1400 shows the location of an aortic valve sinus region 1402 in a patient specific anatomical model of the heart, and image 1410 vortices forming in the sinus region 1402. As shown in FIG. 14, the blood flow simulations recover the known formation of the flow patterns distal to the aortic valve, namely the vortices forming behind each leaflet in the sinus region 1402.

Figure 15:
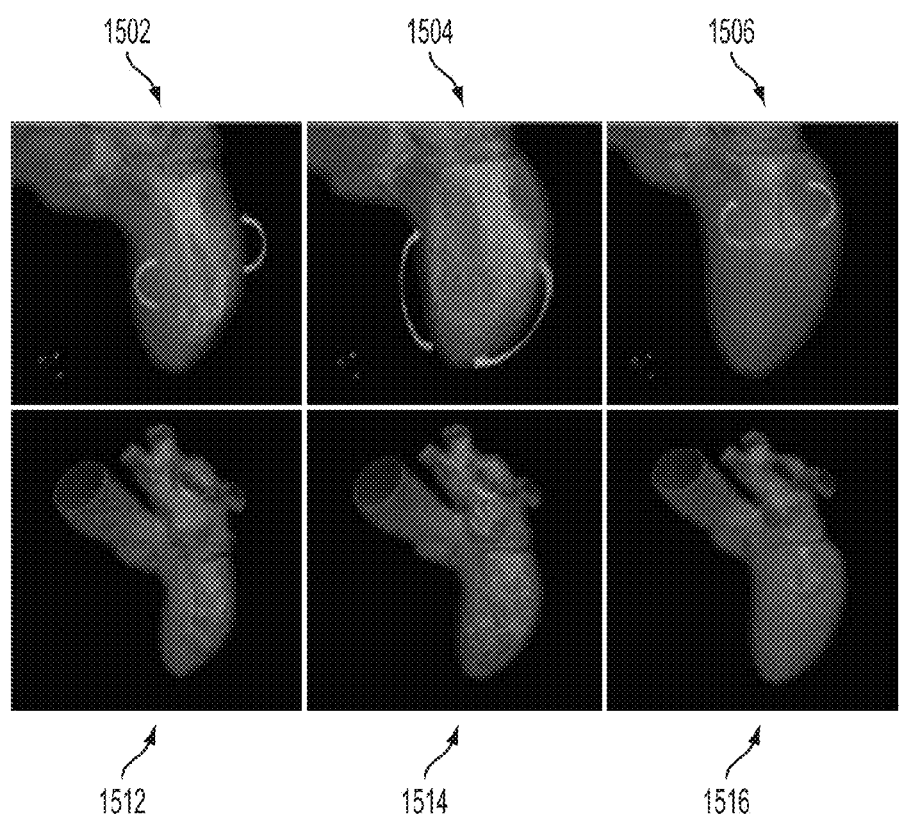
FIG. 15 illustrates hemodynamics simulations of diastolic events and structures.

FIG. 15 illustrates hemodynamics simulations of diastolic events and structures. As shown in FIG. 15, images 1502, 1504, and 1506 show simulated blood flow velocity in the heart in early diastole, mid-diastole, and late mitral filling phases, respectively. Images 1512, 1514, and 1516 show vorticity isosurfaces generated based on the simulated velocities in the early systole, mid-systole, and end-systole phases, respectively. As shown in images 1502 and 1504, the early diastolic (ED) flux begins with the formation of an asymmetric toroidal vortex as the mitral valve opens, that further travels towards the apex at an angle of about 30 degrees with respect to the axis linking the apex and the center of the mitral ring (AMR). Upon hitting the posterior wall of the LV the vortex suffers some dissipation and a change to its axis of about 75 degrees with respect to the AMR. As shown in images 1504 and 1514, this evolves into a vortical pattern that sweeps the apex with a large vortex with a horizontal axis of rotation, which ends with a small vortex rotating in the opposite direction, located just below the aortic valve. The formation of this small vortex is enhanced by the anterior leaflet of the (open) mitral valve. This vortical pattern weakens gradually during mid diastole, becoming barely visible later on. As shown in images 1506 and 1516, the late mitral filling is successfully captured. It creates an extra toroidal vortex that travels downwards and happens concurrently with a small pulmonary vein reflux, which is a normal event.

The flux is qualitatively similar in the right heart. The simulation captured reduced tricuspid flow curve diastasis as compared to the mitral flow curve, as shown in graph 1510 of FIG. 15.

The above described blood flow simulations support the conclusion that tip vortices are being shed from the mitral valve during diastole. This is in partial disagreement with the view that the leaflets align themselves to the flow and therefore shed no vortices and do not steer the flow. This difference is possible due to the enhance heart model of the present invention that includes accurate mitral leaflets. The simulated flow indicates that the mitral valve plays both a steering and a vortex shedding role.

Figure 16:
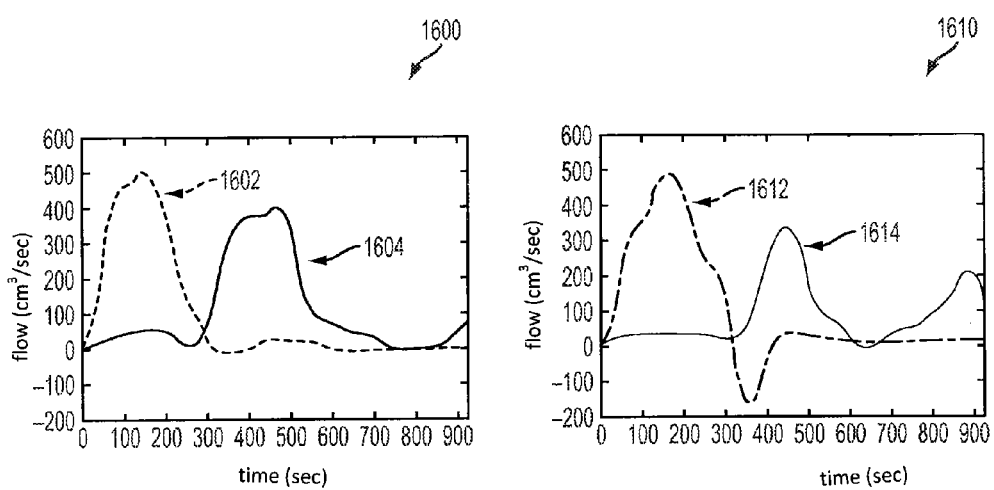
FIG. 16 illustrates graphs showing the temporal flux of blood flow across valve regions over one cardiac cycle.
Figure 17:
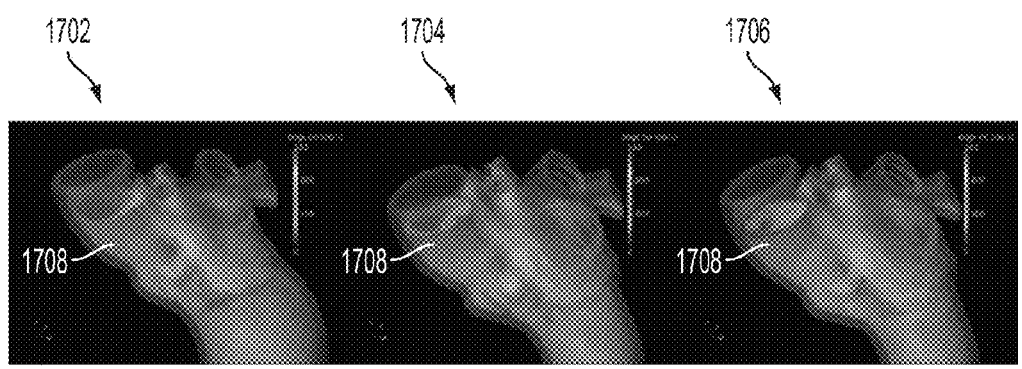
FIGS. 17 and 18 illustrate locations of the slice positions that were used to measure the flow.
Figure 18:
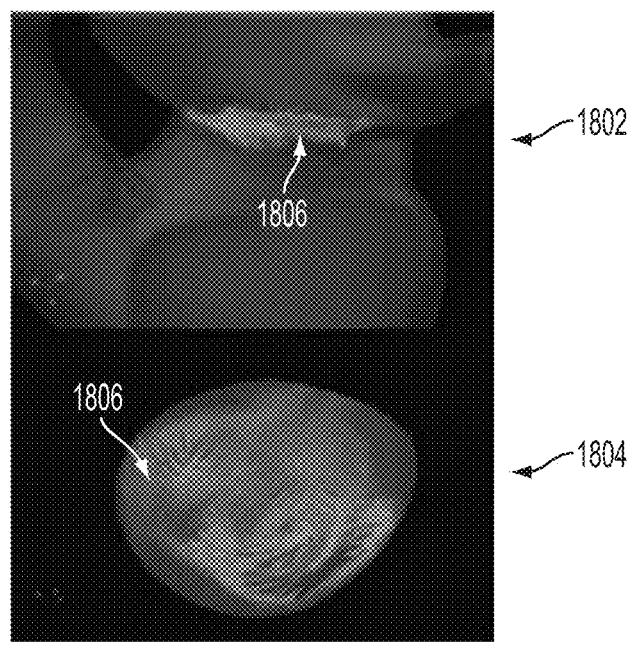

In order to evaluate the accuracy of the hemodynamics simulations, the blood flux was estimated across the valves. Typical PC-MRI flow quantification protocols acquire blood flow across time using MR imaging planes, aligned with the anatomic by the operator. In order to perform a comparison with literature reported observations, this protocol was simulated and the time dependent computed blood flow was quantified in the same fashion using a planed aligned with the valves, as done for PC-MRI. The integral of normal velocity across this plane was calculated and the obtained curves for the examined case are depicted in FIG. 16. FIG. 16 illustrates graphs showing the temporal flux of blood flow across valve regions over one cardiac cycle. Graph 1600 shows the flow in the left heart across aortic valve 1602 and mitral valve 1604 regions. Graph 1610 shows the flow in the right heart across pulmonary valve 1612 and tricuspid valve 1614 regions. The flow shown in graphs 1600 and 1610 is qualitatively similar to the standard flow curves for a normal heart, with the exception of the pulmonary arterial flow, which displays the regurgitation mentioned above. FIGS. 17 and 18 illustrate locations of the slice positions that were used to measure the flow. Images 1702, 1704, and 1706 of FIG. 17 illustrate velocity vectors at a cross-sectional slice 1608 through the aorta at times 0.18, 0.3, and 0.42, respectively, of a 0.92 seconds cardiac cycle. Images 1802 and 1804 show a cross-sectional slice 1806 of a region slightly below the mitral valve.

It can be noted that the clinical practice for measuring average or peak velocities (for example in ultrasound) uses slightly different measurement sites (the aortic site being slightly before the valve region, and the mitral sight being slightly below the mitral valve). However, blood flux (the integral of normal velocity across a given surface) is being measured herein, therefore locations are selected that are meaningfully displaced from (but still close to) clinical measurement sites, such that they: (1) separate the heart model into two topologically disconnected regions along the direction of the flow; and (2) do not cross the valve regions, which would possibly pollute (or at least make more complex) the flux computations.

Since the fluxes are measured just outside the LV, they may include volumetric change components due to the radial motion of the aorta or the atrium. While rather small, these components do show in FIG. 15 as regions of concurrent aortic-mitral (or pulmonary-tricuspid) flow. For the same reason, the isovolumic phases are not exactly quantifiable with this protocol, and therefore are less visible in FIG. 15 (especially the isovolumic relaxation in the LV).

The velocity patterns across the measurement are very complex, as can be seen in FIGS. 17 and 18, and this emphasizes the importance of using correct geographic information, especially for the valves, so that one can minimize the used of incomplete models for inflow or outflow. The inclusion of the geometric models of the valves facilitates the computation of complex flow patterns.

Figure 19:
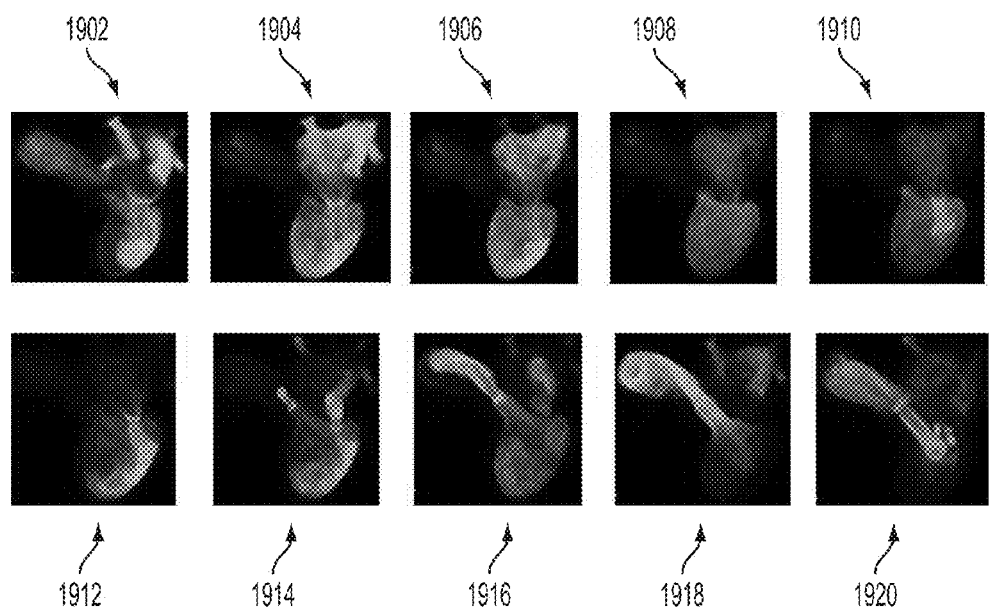
FIG. 19 illustrates a blood flow simulation for a heart with a bicuspid regurgitant aortic valve and a pathological mitral valve.

FIG. 19 illustrates a blood flow simulation for a heart with a bicuspid regurgitant aortic valve and a pathological mitral valve, suffering from both stenosis and regurgitation. Images 1902-1920 illustrates vorticities for one heart cycle resulting from blood flow simulation using a left heart model derived from 4D CT data. In images 1902 and 1904, the left ventricle relaxes, the mitral valve opens, and blood goes into the left ventricle, hitting the wall, due to stenosis. In image 1906 there is relative calm and image 1908 shows diastasis. In images 1910 and 1912, the mitral valve opens for the second time and more blood goes into the left ventricle, again hitting the wall. In images 1914, 1916, and 1918, the left ventricle contracts, the aortic valve opens, blood goes into the aorta, and at the same time the left atrium starts filling. A strong helix is formed due to the bicuspid structure of the aortic valve. In image 1920, the aortic valve closes and the reverse jet indicates regurgitation. As shown in images 1916 and 1918, the blood flow pattern is very different from that of a normal heart in the lower ascending aorta. The systolic jet, normally directed along the centerline of the aorta, is being deflected towards the aortic wall increasing the local wall stress. This could explain why patients with bi-leaflet aortic valve develop aortic root dilation. Furthermore, as shown in images 1902, 1904, and 1912, the pathological mitral valve, suffering from both stenosis and regurgitation, directs the flow toward the posterior LV wall. As shown in images 1914 and 1918, regurgitations of the aortic and mitral valves can be observed during systole and diastole, respectively.

Figure 20:
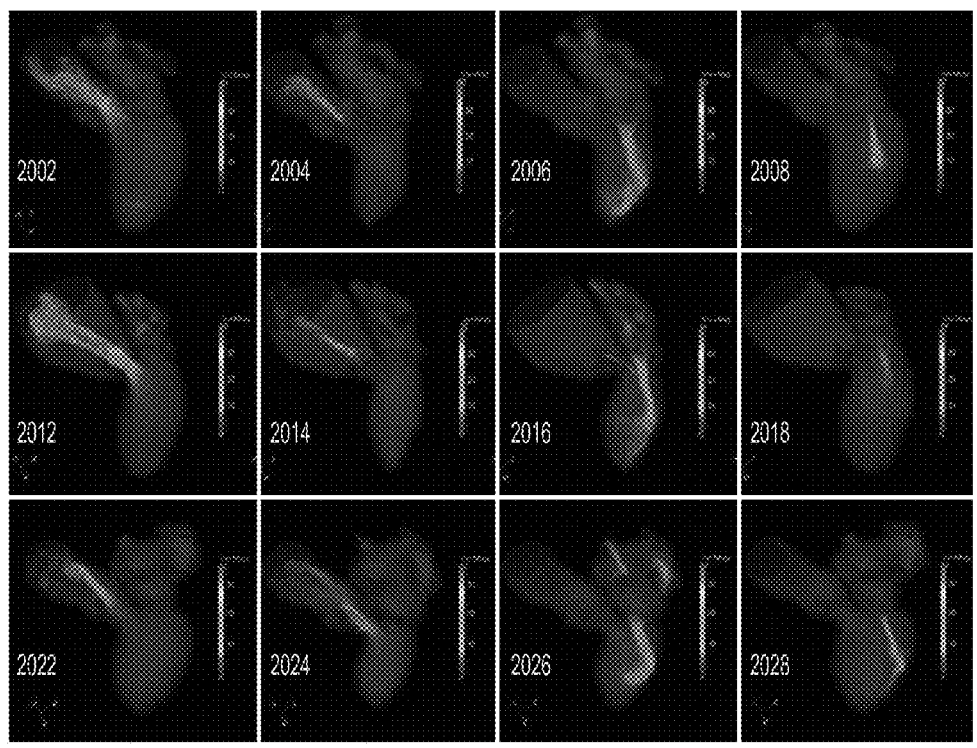
FIG. 20 illustrates a comparison of simulated hemodynamics for a healthy heart and two diseased hearts.

FIG. 20 illustrates a comparison of simulated hemodynamics for a healthy heart and two diseased hearts. As shown in FIG. 20, the first row of images show simulated velocity fields of the left side of the heart for a healthy heart in the early systole phase 2002, late systole phase 2004, early diastole phase 2006, and late diastole filling phase 2008. The second row of images show simulated velocity fields of the left side of the heart for a heart with a dilated aorta in the early systole phase 2012, late systole phase 2014, early diastole phase 2016, and late diastole filling phase 2018. The third row of images show simulated velocity fields of the left side of the heart for a heart with a bicuspid aortic valve in the early systole phase 2022, late systole phase 2024, early diastole phase 2026, and late diastole filling phase 2028.

The diseased hearts feature reflux phenomena in both the valves and pulmonary vein regions. The only reflux for the healthy heart is a small pulmonary venous flow reflux during the late mitral filling, which is a normal phenomenon. The systole is almost twice as short for the healthy heart as compared to the diseased hearts. This is a well known phenomenon, in which diseased hearts develop longer systolic cycles in order to counteract the anatomic faults that led to regurgitations and inefficient blood pumping.

The healthy heart (images 2002-2008) has a fairly short systole (190 ms) in a cardiac cycle of 923 ms. During the systole, the aortic flux was strong, as was the flow in the left atrium. The diastole started with a strong flow through the mitral valve, during which a main rotating vortex formed in the center of the left ventricle, and a smaller vortex formed at the entrance of the aortic valve. The late mitral filling happened concurrently with a small pulmonary vein reflux, which is normal.

The heart with a dilated aorta (images 2012-2018) features a heavily enlarged aorta. Consequently, the aortic valve never closed completely for this particular heart, leading to massive aortic regurgitation during diastole. There was some small but abnormal regurgitation also at the level of the pulmonary veins and mitral region. One interesting fact was that, during the systole, the flow was directed straight toward the abnormally enlarged region of the aorta, which raises the question as to which one contributed to the creation of the other? That is, was it the weak valves that directed the flows obliquely, enlarging the aorta, or was it the aortic weakening that pulled the aortic valves and redirected the flow?

For the heart with the bicuspid aortic valve (images 2022-2028), the deflection of the output jet towards the aortic wall can be observed, which can explain the fact that patients with bi-leaflet aortic valves develop aortic root dilation. In addition, the bicuspid valve is also insufficient, which results in a regurgitation jet towards the left ventricle, observed at the beginning of the diastole (see image 2024). Simulation results also indicate that the aortic and mitral valves were not synchronously opening and closing, which contributed to atrial regurgitation from the ventricle.

Figure 21:
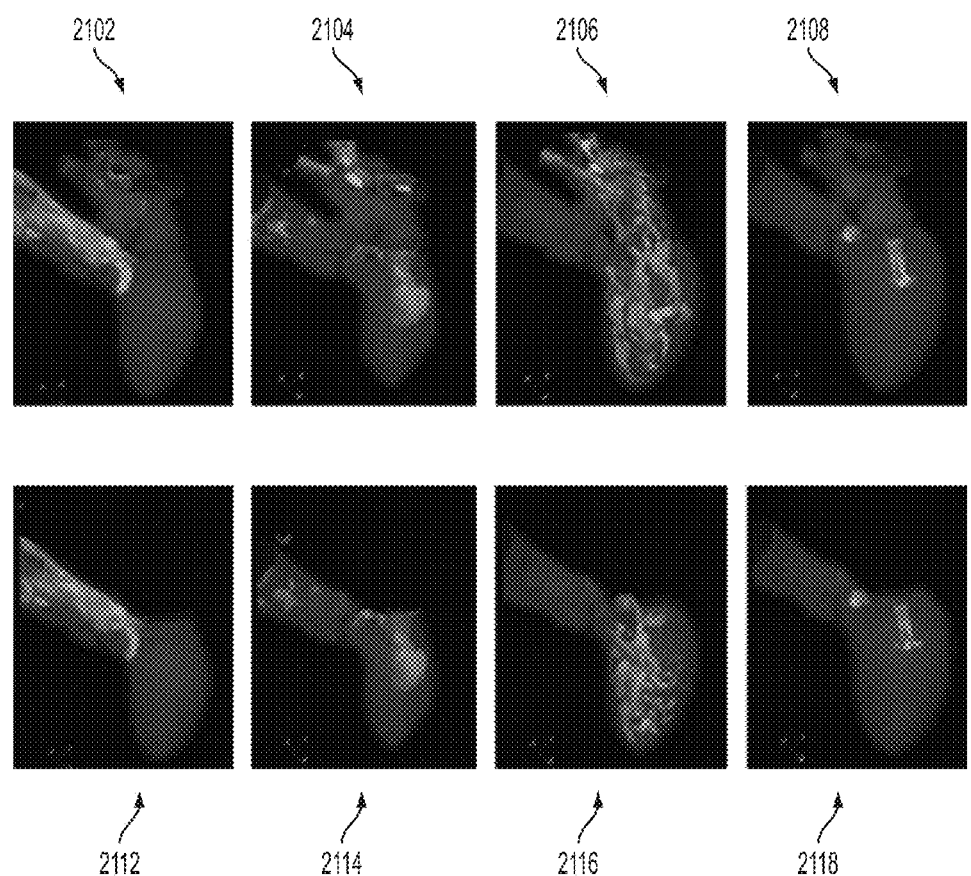
FIG. 21 illustrates the blood flow simulation results with and without the left atrium.

Using the framework described above in FIGS. 1 and 6, simulations were performed using models of the left heart with and without the atrium geometry (all other parameters being equal). FIG. 21 illustrates the blood flow simulation results with and without the left atrium (LA). As shown in FIG. 21, images 2102, 2104, 2106, and 2108 show simulation results with the LA for mid-systole, early diastole, mid-diastole, and mitral filling cardiac stages, respectively. Images 2112, 2114, 2116, and 2118 show simulation results without the LA for mid-systole, early diastole, mid-diastole, and mitral filling cardiac stages, respectively. As shown in images 2102 and 2112, the systolic flow is almost identical with and without the LA. The simulations showed that the vorticity generated mainly from the pulmonary veins, and transported downstream into the LV have a large influence on the simulated blood flow. This is clearly shown in images 2104 and 2114, which also shows that without the LA-to-LV vorticity transport, the simulated flow inside the LV may not differ significantly between models with or without the LA. This is quite interesting, as it hints at a possible solution for modeling realistic boundary conditions without the LA, by including an appropriate model for the vorticity generation inside the LA, and its transport into the LV.

It is to be understood that the hemodynamic simulations described above can also be performed in conjunction with fluid structure interactions to increase the accuracy of the simulations. For example, a model can take in to account more realistic geometry recovery for the walls of the heart components, soft tissue models for the walls of the heart components, and elastic properties for the valves. As described above, fluid structure interaction can be used to estimate biomechanical properties, such as tissue stiffness, of a structure. Such estimated biomechanical properties can be used for diagnostic purposes. For example, by evaluating the stiffness of a structure, such as the aorta, one could assess the risk of ruptures, hypertension, etc. This information could also open the way to more sophisticated models of aneurysm formation, where the biomechanical properties are modified by the pathology.

Figure 22:
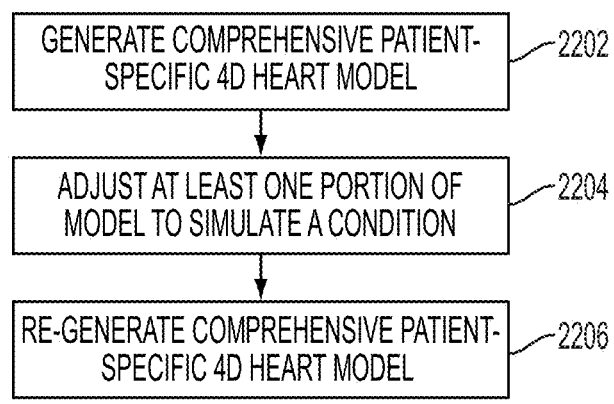
FIG. 22 illustrates a method for predictive planning using a patient-specific comprehensive 4D model according to an embodiment of the present invention.

Returning to FIG. 1, at step 114 virtual therapy planning and/or disease progression prediction can be performed using the comprehensive modeling results. The comprehensive model gives a comprehensive view of the heart function for a patient. This can be used to predict how a certain disease may affect the patient's heart or to predict how the patient will respond to a particular type of therapy or treatment. FIG. 22 illustrates a method for predictive planning using a patient-specific comprehensive 4D model according to an embodiment of the present invention. The method of FIG. 22 can be used to implement step 114 of FIG. 1. Referring to FIG. 22, at step 2202, a comprehensive 4D patient-specific model is generated. In particular, the comprehensive patient-specific model is generated based on 4D medical image data, as described above in steps 104, 106, and 108 of FIG. 1. The comprehensive model for a particular patient can include patient-specific anatomic, morphological, hemodynamic, and biomechanical parameters.

At step 2204, at least a portion of the comprehensive patient-specific 4D model is adjusted to simulate a condition. The condition can be a disease, a therapy or treatment, or any other condition that can affect the parameters of the heart model. In order to simulate a condition, one or more of the anatomical, morphological, hemodynamic, or biomechanical parameters may be adjusted. For example, an anatomical parameter, such as the size of the aorta, may be adjusted to represent the progression of a disease. As described above, various blood flow simulations have been performed on hearts having various diseases, resulting in hemodynamic parameters of diseased hearts. It is possible that certain hemodynamic parameters be adjusted to simulate the presence or severity of a certain pathology of the heart. Furthermore, a biomechanical parameter, such as tissue stiffness, of a certain heart component can be adjusted. For example, the tissue stiffness of the aorta can be adjusted to represent stiffening of the aorta. The model may be also be adjusted in order to virtually test different therapies or treatments using the model to predict a patient's reaction to the therapies. It is to be understood that these examples are not intended to limit the present invention.

At step 2206, the comprehensive patient-specific 4D model is re-generated based on the adjusted portion to predict the effect of the condition on the patient. The method of FIG. 22 can be repeated in order to predict the effect of a condition over a number of time periods, or to predict the effect of multiple different conditions on the patient. For example, the method of FIG. 22 can be repeated to test different treatment alternatives using the patient-specific model in order to select an optimal treatment for the patient. Examples of therapy planning using the comprehensive model are described below. It is to be understood that these examples are not intended to limit the present invention.

In one embodiment, a comprehensive patient-specific model is used for computational decision support for Percutaneous procedures. Percutaneous procedures are becoming increasingly popular due to reduced procedural complications and lower follow-up rates. In such procedures, prosthetic implants are delivered through catheters using transvenous, transarterial, or transapical techniques, which obstruct clinicians from a direct view and direct access to the affected anatomies. Thus, the success of the intervention relies, in a larger part, on intra-operative images, and the experience and skills of the operator, while a suboptimal deployment location of the prosthetic can result in poor hemodynamic performance with sever paravalvular leakages and/or high gradients and a suboptimal effective orifice.

Figure 23A:
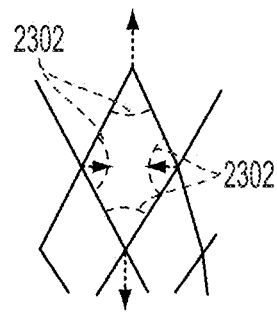
FIGS. 23A-23C illustrate forces acting on the implant model during virtual deployment.
Figure 23B:
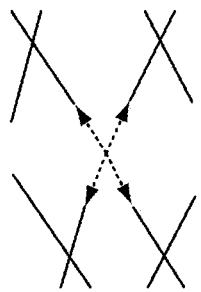
Figure 23C:
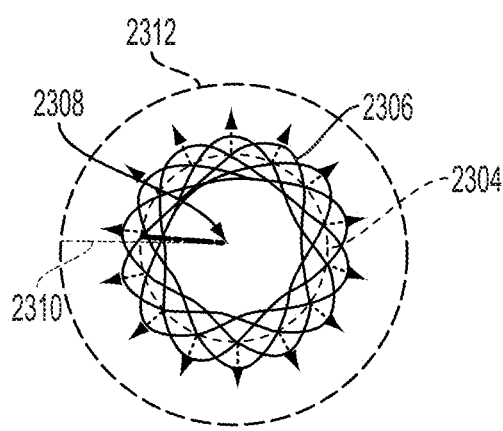

According to an embodiment of the present invention, pre-operative planning for a percutaneous procedure can be implemented using the comprehensive patient specific model. The anatomical model includes the anatomy of the aortic valvular complex, including the aortic valve and the ascending aorta, which is used to perform an in-silico (virtual) delivery of the valve implant based on deformable simplex meshes and geometric constraints. The device is modeled as a stent mesh, which precisely mimics the geometry of the prosthesis, and a computational mesh, which is a superimposed 2-simplex mesh that is used to guide the expansion of the device. The expansion of the device is modeled by balancing external and internal forces as encountered in the actual procedure, using iterative approximation methods. The deformation of the device is described by a finite discretization of a second order differential equation. FIGS. 23A-23C illustrate the forces acting on the implant model during virtual deployment. The arrows of FIG. 23A represent the $f_{angle}$, which enforces characteristic angles 2302 at the strut joints. The arrows of FIG. 23B represent $f_{length}$, which maintains the strut lengths. FIG. 23C shows a short axis cross-section of the stent mesh. The arrows of FIG. 23C represent $f_{circ}$, which enforces the circumference 2304, while $f_{ext}$ dampens and eliminates all of the forces acting along the stent mesh normal weighted by a ratio of the distance 2306 from the strut joint the stent centroid 2308 and the distance 2310 from the vessel wall 2312 to the stent centroid 2308.

Based on the forces shown in FIGS. 23A-23C, the implantation of the prosthesis is simulated virtually. This technique can be used to predict the best implant type, size, and deployment location and orientation under various treatment hypotheses. In addition to predicting the anatomical fit of the prothesis, it is also possible to re-generate the comprehensive model, and perform hemodynamic simulations and fluid structure interactions with the virtually implanted prosthesis.

The predictive power of the model-based in-silico valve replacement was evaluated on 20 patients with pre-operative and post-operative 3D cardiac scans, each by comparing the prediction result with a ground truth model manually fitted to the real device imaging in the postoperative data. With an accuracy below 2 mm at the annular level, the potential was demonstrated for this approach to support preoperative planning by finding the best implant type, size, and deployment location and orientation via in-silico implantation under various treatment hypotheses until the optimal predicted performance is observed.

Figure 24:
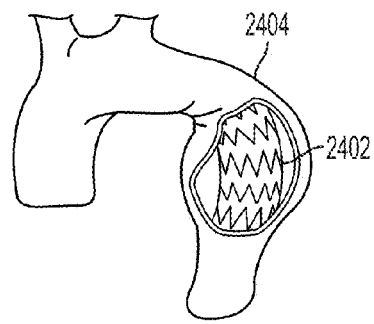
FIG. 24 illustrates a simulation of stent deployment at an aneurysm in the aorta.

Another possible application for virtual therapy planning using the comprehensive patient-specific 4D model is for simulation of stent deployment at an aneurysm in the aorta. FIG. 24 illustrates a simulation of stent deployment at an aneurysm in the aorta. As shown in FIG. 24, a mesh 2402 representing a stent is virtually implanted in the aorta 2404 at an aneurysm. The force generated by the deployment of the stent deforms the aortic wall locally at the anchored sections of the stent. The fluid structure interactions are used to model this deformation. Modeling this deformation is crucial to assess the strength and the stent anchoring and its impact on the blood flow. With such a framework, a cardiologist can test different stent designs and choose the optimal stent for the patient.

Figure 25:
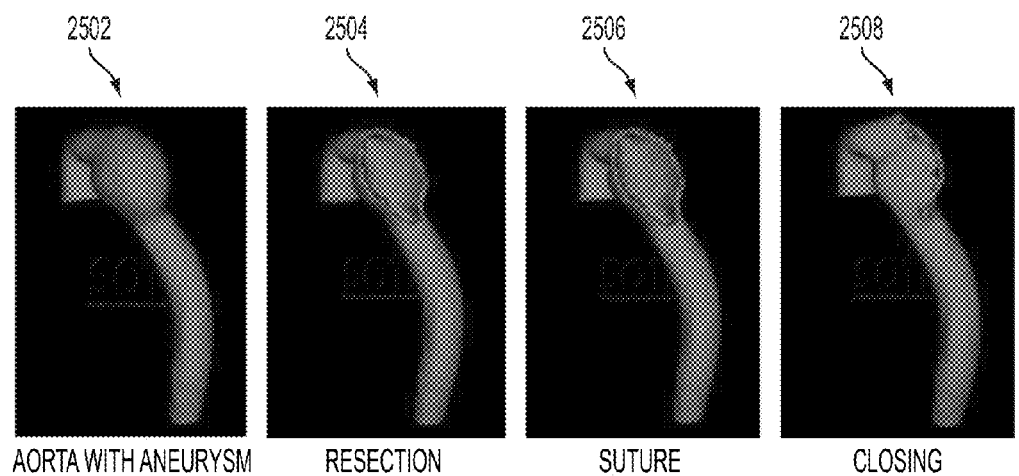
FIG. 25 illustrates a virtual aneurysm resection.

Another possible application for virtual therapy planning using the comprehensive patient-specific 4D model is to virtually resection an aortic aneurysm. In particular, this application simulates, in silico, the effects of a resection of an aneurysm the blood flow. The patient-specific model of the aorta (including personalized geometry and biomechanical parameters) can be loaded in a real-time soft-tissue intervention platform. With that platform, a user can perform a virtual intervention, including a resection, closure, and suture. FIG. 25 illustrates a virtual aneurysm resection. As illustrated in FIG. 25, image 2502 shows an aorta with an aneurysm, image 2504 shows a resection of the aneurysm, image 2506 shows a suture of the resection, and image 2508 shows closing the resection. The FSI model is then performed on the postoperative geometry to simulate the postoperative blood flow. The proposed methodology is validated by adjusting the model from preoperative data and testing it on postoperative data. This proposed framework can help with the preparation of a surgical intervention by defining the exact sections to be removed.

Figure 26:
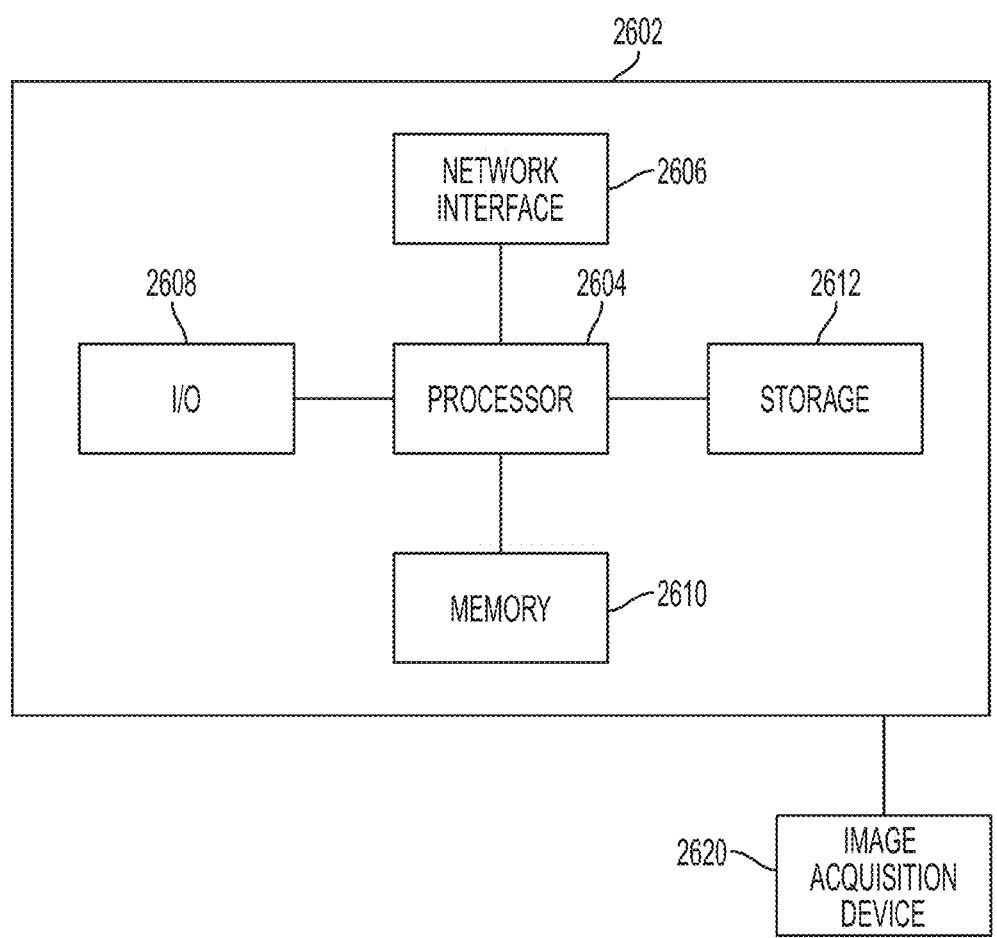
FIG. 26 is a high-level block diagram of a computer capable of implementing the present invention.

The above-described methods for comprehensive modeling of the heart, generating a patient-specific 4D anatomical model of the heart, simulating blood flow in the heart, simulating fluid structure interactions, and predictive planning using a comprehensive heart model may be implemented on a computer using well-known computer processors, memory units, storage devices, computer software, and other components. A high-level block diagram of such a computer is illustrated in FIG. 26. Computer 702 contains a processor 704, which controls the overall operation of the computer 2602 by executing computer program instructions which define such operation. The computer program instructions may be stored in a storage device 2612 (e.g., magnetic disk) and loaded into memory 2610 when execution of the computer program instructions is desired. Thus, the steps of the methods of FIGS. 1, 3, 6, 8, and 22 may be defined by the computer program instructions stored in the memory 2610 and/or storage 2612 and controlled by the processor 2604 executing the computer program instructions. An image acquisition device 2620, such as a CT scanning device, MR scanning device, ultrasound device, etc., can be connected to the computer 2602 to input image data to the computer 2602. It is possible to implement the image acquisition device 2620 and the computer 2602 as one device. It is also possible that the image acquisition device 2620 and the computer 2602 communicate wirelessly through a network. The computer 2602 also includes one or more network interfaces 2606 for communicating with other devices via a network. The computer 2602 also includes other input/output devices 2608 that enable user interaction with the computer 2602 (e.g., display, keyboard, mouse, speakers, buttons, etc.). Such input/output devices 2608 may be used in conjunction with a set of computer programs as an annotation tool to annotate volumes received from the image acquisition device 2620. One skilled in the art will recognize that an implementation of an actual computer could contain other components as well, and that FIG. 26 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for simulating blood flow in the heart based on 4D medical image data, comprising:
generating a patient-specific 4D anatomical model of the heart from the 4D medical imaging data; and
simulating blood flow in the heart by solving Navier-Stokes equations constrained by the patient-specific 4D anatomical model at each of a plurality of time steps in a heart cycle using a level set framework, wherein the simulating blood flow in the heart comprises:
imposing no-slip boundary conditions to a fluid region of the anatomical model based on a location of a zero level of a level set function used to embed the patient-specific 4D anatomical model in a computational domain.

2. The method of claim 1, wherein the patient-specific 4D anatomical model of the heart comprises a plurality of heart components, and the step of simulating blood flow in the heart by solving Navier-Stokes equations constrained by the patient-specific 4D anatomical model at each of a plurality of time steps in a heart cycle using a level set framework comprises:
simulating blood flow separately in one or more of the plurality of heart components of the patient-specific 4D anatomical model.

3. The method of claim 1, wherein the patient-specific 4D anatomical model of the heart comprises a plurality of heart components, and the step of simulating blood flow in the heart by solving Navier-Stokes equations constrained by the patient-specific 4D anatomical model at each of a plurality of time steps in a heart cycle using a level set framework comprises:
simulating blood flow simultaneously in each of the plurality of heart components of the patient-specific 4D anatomical model.

4. The method of claim 1, wherein the patient-specific 4D anatomical model of the heart comprises a plurality of heart components, and the step of simulating blood flow in the heart by solving Navier-Stokes equations constrained by the patient-specific 4D anatomical model at each of a plurality of time steps in a heart cycle using a level set framework comprises, for each of the plurality of time steps:
calculating convective updates to a level set function and velocity based on the location of the patient-specific 4D anatomical model at the current time step;
calculating a semi-implicit update for the velocity representing a viscous force contribution at the current time step;
calculating a pressure update at the current time step by solving a Poisson equation with Neumann boundary conditions; and
calculating a new velocity update for the current time step based on the semi-implicit velocity update and the pressure update.

5. The method of claim 1, wherein the patient-specific 4D anatomical model comprises a sequence of patient-specific 3D anatomical models of the heart over the heart cycle, and the step of simulating blood flow in the heart by solving Navier-Stokes equations constrained by the patient-specific 4D anatomical model at each of a plurality of time steps in a heart cycle using a level set framework comprises:
interpolating the sequence of patient-specific 3D anatomical models to derive a location of the patient-specific 4D anatomical model at at least one of the plurality of time steps.

6. The method of claim 1, wherein the step of generating a patient-specific 4D anatomical model of the heart from the 4D medical imaging data comprises:
generating a patient specific multi-scale anatomical model of at least one heart component, the multi-scale anatomical model including a coarse anatomical model of the at least one heart component and a fine anatomical model of the at least one heart component.

7. The method of claim 6, wherein the step of simulating blood flow in the heart by solving Navier-Stokes equations constrained by the patient-specific 4D anatomical model at each of a plurality of time steps in a heart cycle using a level set framework comprises:
  simulating the blood flow in the at least one heart component by solving Navier-Stokes equations constrained by the fine anatomical model of the at least one heart component.

8. The method of claim 7, wherein the at least one heart component comprises the left ventricle and the fine anatomical model of the left ventricle includes the papillary muscles and trabeculae.

9. A method for comprehensive patient-specific modeling of the heart based on 4D medical image data, comprising:
  generating a patient-specific 4D anatomical model of the heart from the 4D medical imaging data;
  simulating blood flow in at least one heart component of the patient-specific 4D anatomical model at a current time step by solving Navier-Stokes equations constrained by the location of the at least one heart component at the current time step using a level set framework;
  calculating a deformation of the at least one heart component at the current time step based on the simulated blood flow at the current time step; and
  repeating the simulating and calculating steps for a plurality of time steps, wherein the current location of the at least one heart component at the current time step is determined at least in part based on the deformation of the at least one heart component calculated at a previous time step.

10. The method of claim 9, further comprising:
  comparing the calculated deformation of the at least one heart component with an observed deformation of the at least one heart component in the 4D medical imaging data to determine a biomechanical parameter of the at least one heart component.

11. The method of claim 9, wherein the at least one heart component is the aorta.

12. The method of claim 9, wherein the step of simulating blood flow in at least one heart component of the patient-specific 4D anatomical model at a current time step by solving Navier-Stokes equations constrained by the location of the at least one heart component at the current time step using a level set framework comprises:
  calculating pressure at a wall interface of the at least one heart component at the current time step due to the simulated blood flow in the at least one heart component.

13. The method of claim 12, wherein the step of calculating a deformation of the at least one heart component at the current time step based on the simulated blood flow at the current time step comprises:
  calculating a deformation of a wall of the at least one heart component due to the pressure at the wall interface of the at least one heart component.

14. The method of claim 9, wherein the step of calculating a deformation of the at least one heart component at the current time step based on the simulated blood flow at the current time step comprises:
  calculating the deformation of the at least one heart component based on an internal force that models passive properties of the tissue of the at least one heart component and an external force that models loading generated by the blood flow inside the at least one heart component.

15. A method of predictive planning using a comprehensive patient-specific 4D heart model, comprising:
  generating a comprehensive patient-specific 4D model of the heart from 4D medical imaging data;
  adjusting a portion of the comprehensive patient-specific 4D model to simulate a condition; and
  re-generating the comprehensive patient-specific 4D model of the heart to simulate the effect of the adjusted portion on the comprehensive patient-specific 4D model.

16. The method of claim 15, wherein the step of adjusting a portion of the comprehensive patient-specific 4D model to simulate a condition comprises:
  adjusting an anatomical parameter of the comprehensive patient-specific 4D model.

17. The method of claim 15, wherein the step of adjusting a portion of the comprehensive patient-specific 4D model to simulate a condition comprises:
  adjusting a hemodynamic parameter of the comprehensive patient-specific 4D model.

18. The method of claim 15, wherein the step of adjusting a portion of the comprehensive patient-specific 4D model to simulate a condition comprises:
  adjusting a biomechanical parameter of the comprehensive patient-specific 4D model.

19. The method of claim 15, wherein the step of adjusting a portion of the comprehensive patient-specific 4D model to simulate a condition comprises:
  adjusting at least one of an anatomical parameter, a hemodynamic parameter, and a biomechanical parameter of the comprehensive patient-specific 4D model to simulate progression of a disease in the heart.

20. The method of claim 15, wherein the step of adjusting a portion of the comprehensive patient-specific 4D model to simulate a condition comprises:
  adjusting a portion of the comprehensive patient-specific 4D model to virtually simulate applying a therapy to a corresponding portion of the heart.

21. The method of claim 20, wherein the step of adjusting a portion of the comprehensive patient-specific 4D model to virtually simulate applying a therapy to a corresponding portion of the heart comprises:
  virtually simulating percutaneous artificial valve implantation in the comprehensive patient-specific 4D model.

22. The method of claim 20, wherein the step of adjusting a portion of the comprehensive patient-specific 4D model to virtually simulate applying a therapy to a corresponding portion of the heart comprises:
  virtually simulating stent deployment at an aneurysm in a portion of the comprehensive patient-specific 4D model.

23. The method of claim 20, wherein the step of adjusting a portion of the comprehensive patient-specific 4D model to virtually simulate applying a therapy to a corresponding portion of the heart comprises:
  virtually simulating resection of an aneurysm in a portion of the comprehensive patient-specific 4D model.

24. The method of claim 23, wherein the step of re-generating the comprehensive patient-specific 4D model of the heart to simulate the effect of the adjusted portion on the comprehensive patient-specific 4D model comprises:
  simulating blood flow and fluid structure interactions in the portion of the comprehensive patient-specific 4D model based on the simulated resection of the aneurysm.

25. An apparatus for simulating blood flow in the heart based on 4D medical image data, comprising:
  means for generating a patient-specific 4D anatomical model of the heart from the 4D medical imaging data; and
  means for simulating blood flow in the heart by solving Navier-Stokes equations constrained by the patient-specific 4D anatomical model at each of a plurality of time steps in a heart cycle using a level set framework, wherein the means for simulating blood flow comprises:
means for imposing no-slip boundary conditions to a fluid region of the anatomical model based on a location of a zero level of a level set function used to embed the patient-specific 4D anatomical model in a computational domain.

26. The apparatus of claim 25, wherein the patient-specific 4D anatomical model of the heart comprises a plurality of heart components, and the means for simulating blood flow in the heart by solving Navier-Stokes equations constrained by the patient-specific 4D anatomical model at each of a plurality of time steps in a heart cycle using a level set framework comprises:
means for calculating convective updates to a level set function and velocity based on the location of the patient-specific 4D anatomical model at a current time step;
means for calculating a semi-implicit update for the velocity representing a viscous force contribution at the current time step;
means for calculating a pressure update at the current time step by solving a Poisson equation with Neumann boundary conditions; and
means for calculating a new velocity update for the current time step based on the semi-implicit velocity update and the pressure update.

27. The apparatus of claim 25, wherein the means for generating a patient-specific 4D anatomical model of the heart from the 4D medical imaging data comprises:
means for generating a patient specific multi-scale anatomical model of at least one heart component, the multi-scale anatomical model including a coarse anatomical model of the at least one heart component and a fine anatomical model of the at least one heart component.

28. The apparatus of claim 27, wherein the means for simulating blood flow in the heart by solving Navier-Stokes equations constrained by the patient-specific 4D anatomical model at each of a plurality of time steps in a heart cycle using a level set framework comprises:
means for simulating the blood flow in the at least one heart component by solving Navier-Stokes equations constrained by the fine anatomical model of the at least one heart component.

29. An apparatus for comprehensive patient-specific modeling of the heart based on 4D medical image data, comprising:
means for generating a patient-specific 4D anatomical model of the heart from the 4D medical imaging data;
means for simulating blood flow in at least one heart component of the patient-specific 4D anatomical model at a current time step by solving Navier-Stokes equations constrained by the location of the at least one heart component at the current time step using a level set framework, wherein the current location of the at least one heart component at the current time step is determined at least in part based on a deformation of the at least one heart component calculated at a previous time step; and
means for calculating a deformation of the at least one heart component at the current time step based on the simulated blood flow at the current time step.

30. The apparatus of claim 29, further comprising:
means for comparing the calculated deformation of the at least one heart component with an observed deformation of the at least one heart component in the 4D medical imaging data to determine a biomechanical parameter of the at least one heart component.

31. The apparatus of claim 29, wherein the means for simulating blood flow in at least one heart component of the patient-specific 4D anatomical model at a current time step by solving Navier-Stokes equations constrained by the location of the at least one heart component at the current time step using a level set framework comprises:
means for calculating pressure at a wall interface of the at least one heart component at the current time step due to the simulated blood flow in the at least one heart component.

32. The apparatus of claim 31, wherein the means for calculating a deformation of the at least one heart component at the current time step based on the simulated blood flow at the current time step comprises:
means for calculating a deformation of a wall of the at least one heart component due to the pressure at the wall interface of the at least one heart component.

33. The apparatus of claim 29, wherein the means for calculating a deformation of the at least one heart component at the current time step based on the simulated blood flow at the current time step comprises:
means for calculating the deformation of the at least one heart component based on an internal force that models passive properties of the tissue of the at least one heart component and an external force that models loading generated by the blood flow inside the at least one heart component.

34. An apparatus for predictive planning using a comprehensive patient-specific 4D heart model, comprising:
means for generating a comprehensive patient-specific 4D model of the heart from 4D medical imaging data;
means for adjusting a portion of the comprehensive patient-specific 4D model to simulate a condition; and
means for re-generating the comprehensive patient-specific 4D model of the heart to simulate the effect of the adjusted portion on the comprehensive patient-specific 4D model.

35. The apparatus of claim 34, wherein the means for adjusting a portion of the comprehensive patient-specific 4D model to simulate a condition comprises:
means for adjusting at least one of an anatomical parameter, a hemodynamic parameter, and a biomechanical parameter of the comprehensive patient-specific 4D model.

36. The apparatus of claim 34, wherein the means for adjusting a portion of the comprehensive patient-specific 4D model to simulate a condition comprises:
means for adjusting at least one of an anatomical parameter, a hemodynamic parameter, and a biomechanical parameter of the comprehensive patient-specific 4D model to simulate progression of a disease in the heart.

37. The apparatus of claim 34, wherein the means for adjusting a portion of the comprehensive patient-specific 4D model to simulate a condition comprises:
means for adjusting a portion of the comprehensive patient-specific 4D model to virtually simulate applying a therapy to a corresponding portion of the heart.

38. A non-transitory computer readable medium encoded with computer executable instructions for simulating blood flow in the heart based on 4D medical image data, the computer executable instructions defining steps comprising:
generating a patient-specific 4D anatomical model of the heart from the 4D medical imaging data; and
simulating blood flow in the heart by solving Navier-Stokes equations constrained by the patient-specific 4D anatomical model at each of a plurality of time steps in a heart cycle using a level set framework, wherein the simulating blood flow comprises:
imposing no-slip boundary conditions to a fluid region of the anatomical model based on a location of a zero level of a level set function used to embed the patient-specific 4D anatomical model in a computational domain.

39. The computer readable medium of claim 38, wherein the patient-specific 4D anatomical model of the heart comprises a plurality of heart components, and the computer executable instructions defining the step of simulating blood flow in the heart by solving Navier-Stokes equations constrained by the patient-specific 4D anatomical model at each of a plurality of time steps in a heart cycle using a level set framework comprise computer executable instructions defining the steps of, for each of the plurality of time steps:
calculating convective updates to a level set function and velocity based on the location of the patient-specific 4D anatomical model at the current time step;
calculating a semi-implicit update for the velocity representing a viscous force contribution at the current time step;
calculating a pressure update at the current time step by solving a Poisson equation with Neumann boundary conditions; and
calculating a new velocity update for the current time step based on the semi-implicit velocity update and the pressure update.

40. The computer readable medium of claim 38, wherein the computer executable instructions defining the step of generating a patient-specific 4D anatomical model of the heart from the 4D medical imaging data comprise computer executable instructions defining the step of:
generating a patient specific multi-scale anatomical model of at least one heart component, the multi-scale anatomical model including a coarse anatomical model of the at least one heart component and a fine anatomical model of the at least one heart component.

41. The computer readable medium of claim 40, wherein the computer executable instructions defining the step of simulating blood flow in the heart by solving Navier-Stokes equations constrained by the patient-specific 4D anatomical model at each of a plurality of time steps in a heart cycle using a level set framework comprise computer executable instructions defining the step of:
simulating the blood flow in the at least one heart component by solving Navier-Stokes equations constrained by the fine anatomical model of the at least one heart component.

42. A non-transitory computer readable medium encoded with computer executable instructions for comprehensive patient-specific modeling of the heart based on 4D medical image data, the computer executable instructions defining steps comprising:
generating a patient-specific 4D anatomical model of the heart from the 4D medical imaging data;
simulating blood flow in at least one heart component of the patient-specific 4D anatomical model at a current time step by solving Navier-Stokes equations constrained by the location of the at least one heart component at the current time step using a level set framework;
calculating a deformation of the at least one heart component at the current time step based on the simulated blood flow at the current time step; and
repeating the simulating and calculating steps for a plurality of time steps, wherein the current location of the at least one heart component at the current time step is determined at least in part based on the deformation of the at least one heart component calculated at a previous time step.

43. The computer readable medium of claim 42, further comprising computer executable instructions defining the step of:
comparing the calculated deformation of the at least one heart component with an observed deformation of the at least one heart component in the 4D medical imaging data to determine a biomechanical parameter of the at least one heart component.

44. The computer readable medium of claim 42, wherein the computer executable instructions defining the step of simulating blood flow in at least one heart component of the patient-specific 4D anatomical model at a current time step by solving Navier-Stokes equations constrained by the location of the at least one heart component at the current time step using a level set framework comprise computer executable instructions defining the step of:
calculating pressure at a wall interface of the at least one heart component at the current time step due to the simulated blood flow in the at least one heart component.

45. The computer readable medium of claim 44, wherein the computer executable instructions defining the step of calculating a deformation of the at least one heart component at the current time step based on the simulated blood flow at the current time step comprise computer executable instructions defining the step of:
calculating a deformation of a wall of the at least one heart component due to the pressure at the wall interface of the at least one heart component.

46. The computer readable medium of claim 42, wherein the computer executable instructions defining the step of calculating a deformation of the at least one heart component at the current time step based on the simulated blood flow at the current time step comprise computer executable instructions defining the step of:
calculating the deformation of the at least one heart component based on an internal force that models passive properties of the tissue of the at least one heart component and an external force that models loading generated by the blood flow inside the at least one heart component.

47. A non-transitory computer readable medium encoded with computer executable instructions for predictive planning using a comprehensive patient-specific 4D heart model, the computer executable instructions defining steps comprising:
generating a comprehensive patient-specific 4D model of the heart from 4D medical imaging data;
adjusting a portion of the comprehensive patient-specific 4D model to simulate a condition; and
re-generating the comprehensive patient-specific 4D model of the heart to simulate the effect of the adjusted portion on the comprehensive patient-specific 4D model.

48. The computer readable medium of claim 47, wherein the computer executable instructions defining the step of adjusting a portion of the comprehensive patient-specific 4D model to simulate a condition comprise computer executable instructions defining the step of:
adjusting at least one of an anatomical parameter, a hemodynamic parameter, and a biomechanical parameter of the comprehensive patient-specific 4D model.

49. The computer readable medium of claim 47, wherein the computer executable instructions defining the step of adjusting a portion of the comprehensive patient-specific 4D model to simulate a condition comprise computer executable instructions defining the step of:

adjusting at least one of an anatomical parameter, a hemodynamic parameter, and a biomechanical parameter of the comprehensive patient-specific 4D model to simulate progression of a disease in the heart.

50. The computer readable medium of claim 47, wherein the computer executable instructions defining the step of adjusting a portion of the comprehensive patient-specific 4D model to simulate a condition comprise computer executable instructions defining the step of:

adjusting a portion of the comprehensive patient-specific 4D model to virtually simulate applying a therapy to a corresponding portion of the heart.

* * * * *